(12) United States Patent
Savage

(10) Patent No.: US 10,155,788 B2
(45) Date of Patent: Dec. 18, 2018

(54) CATIONIC STEROIDAL ANTIMICROBIAL PRODRUG COMPOSITIONS AND USES THEREOF

(71) Applicant: Paul B. Savage, Mapleton, UT (US)

(72) Inventor: Paul B. Savage, Mapleton, UT (US)

(73) Assignee: BRIGHAM YOUNG UNIVERSITY, Provo, UT (US)

(*) Notice: Subject to any disclaimer, the term of this patent is extended or adjusted under 35 U.S.C. 154(b) by 87 days.

(21) Appl. No.: 14/875,953

(22) Filed: Oct. 6, 2015

(65) Prior Publication Data

US 2016/0096864 A1 Apr. 7, 2016

Related U.S. Application Data

(60) Provisional application No. 62/061,087, filed on Oct. 7, 2014, provisional application No. 62/192,221, filed on Jul. 14, 2015.

(51) Int. Cl.
*A61K 31/575* (2006.01)
*C07J 41/00* (2006.01)
*A61K 45/06* (2006.01)

(52) U.S. Cl.
CPC ......... *C07J 41/0055* (2013.01); *A61K 31/575* (2013.01); *A61K 45/06* (2013.01); *C07J 41/0061* (2013.01); *C07J 41/0094* (2013.01)

(58) Field of Classification Search
CPC .................................................. A61K 31/575
See application file for complete search history.

(56) References Cited

U.S. PATENT DOCUMENTS 4,248,236 A 2/1981 Linder
4,296,206 A * 10/1981 Simons, Jr. ............ A61K 31/57
435/375

(Continued)

FOREIGN PATENT DOCUMENTS

CN 101378761 3/2009
CN 102172356 9/2011

(Continued)

OTHER PUBLICATIONS

Alafort et al., "Lys and Arg in UBI: A specific site for a stable Tc-99m complex?", Nuclear Medicine and Biology 30 (2003) 605-615.

(Continued)

*Primary Examiner* — Benjamin J Packard
(74) *Attorney, Agent, or Firm* — Workman Nydegger

(57) ABSTRACT

Prodrugs or pharmaceutically acceptable salts, stereoisomers, solvates, or polymorphs thereof include a pharmaceutically and/or diagnostically active cationic steroidal antimicrobial (hereinafter "CSA") compound or pharmaceutically acceptable salt, stereoisomer, solvate, or polymorph thereof, and one or more cleavable groups (C.G.). Some embodiments include a CSA compound prepared in an inactive or less active form and that is capable of conversion to a fully active form upon administration to a subject, upon preparation of a pharmaceutical formulation containing the CSA composition, and/or upon exposure to physiological conditions. Pharmaceutical compositions include the prodrug or pharmaceutically acceptable salt, stereoisomer, solvate, or polymorph thereof and one or more pharmaceutically acceptable excipients. Methods of treatment of bacterial infections in a patient in need utilize prodrugs or pharmaceutically acceptable salts, stereoiso- (Continued)

mers, solvates, polymorphs thereof and/or the pharmaceutical compositions described herein.

29 Claims, 2 Drawing Sheets

(56) References Cited

U.S. PATENT DOCUMENTS

| | | | |
|---|---|---|---|
| 4,661,341 A | 4/1987 | Benedict et al. |
| 4,723,950 A | 2/1988 | Lee |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 6,117,332 A | 9/2000 | Hatch et al. |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 7/2005 | Shulze et al. |
| 7,282,214 B2 | 10/2007 | Willcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,527,883 B2 | 12/2016 | Savage et al. |
| 2002/0091278 A1 | 7/2002 | Savage et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0091376 A1 | 4/2011 | Savage et al. |
| 2011/0123624 A1 | 5/2011 | Zasloff |
| 2011/0135742 A1 | 6/2011 | Kim et al. |
| 2011/0230589 A1 | 9/2011 | Maggio et al. |
| 2012/0088733 A1 | 4/2012 | Kim et al. |
| 2012/0107382 A1 | 5/2012 | Savage et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0040265 A1 | 2/2013 | Park et al. |
| 2013/0236619 A1 | 9/2013 | Savage |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0315873 A1 | 10/2014 | Beus et al. |
| 2014/0336131 A1 | 11/2014 | Savage et al. |
| 2014/0363780 A1 | 12/2014 | Vazquez et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2016/0193232 A1 | 3/2016 | Beus et al. |
| 2016/0199390 A1 | 3/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |

FOREIGN PATENT DOCUMENTS

| | | |
|---|---|---|
| DE | 1037074 | 8/1958 |
| EP | 0341951 | 11/1989 |
| EP | 1208844 | 5/2002 |
| EP | 1219631 | 7/2002 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |

(56) References Cited

FOREIGN PATENT DOCUMENTS

| | | |
|---|---|---|
| JP | 2011527702 | 11/2011 |
| JP | 2014500741 | 1/2014 |
| WO | WO 1995024415 | 9/1995 |
| WO | WO 9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO2003015757 | 2/2003 |
| WO | WO03090799 | 11/2003 |
| WO | WO2004082588 | 9/2004 |
| WO | WO2004112852 | 12/2004 |
| WO | WO2007089903 | 8/2007 |
| WO | WO2007089906 | 8/2007 |
| WO | WO2007089907 | 8/2007 |
| WO | WO2007134176 | 11/2007 |
| WO | WO2008038965 | 4/2009 |
| WO | WO2009079066 | 6/2009 |
| WO | WO2009144708 | 12/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO2011109704 | 9/2011 |
| WO | WO2012061651 | 5/2012 |
| WO | WO2013029055 | 2/2013 |
| WO | WO2013029059 | 2/2013 |
| WO | WO2013109236 | 7/2013 |
| WO | 2013167743 | 11/2013 |
| WO | 2014062960 | 4/2014 |

OTHER PUBLICATIONS

Brown, "Bioisosteres in Medicinal Chemistry, First Edition", ediated by Nathan Brown, 2012, Ch. 2 Classical Bioisosteres, pp. 1-52.
Fichna et al., "Synthesis of Target-Specific Radiolabeled Peptides for Diagnostic Imaging", Bioconjugate Chem., 2003, 14, 3-17, American Chemical Society.
International Search Report for PCT Application No. PCT/US2015/046412 dated Dec. 1, 2015.
International Search Report for PCT Application No. PCT/US2015/054434 dated Dec. 23, 2015.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lankinen et al., "Ga-Dota-Peptide Targeting VAP-1 for In Vivo Evaluation of Inflammatory and Infetious Bone Conditions", 52nd Annual Meeting of the Orthopaedic Research Society.
Li et al., "Incremental conversin of Outer-Membrane Permeabilizers into Potent Antibiotics for Gram-Negative Bacteria", J. Am. Chem. Soc. 1999, 121, 9310-940.
Lowe et al., "Effect of Hydrophobicity of a Drug on its Release from Hydrogels with Different Topological Structures" Journal of Polymer Science (1999) 73: 1031-1039 (9 pages).
Massoud et al., "Molecular imaging in living subjects: seeing fundamental biological processes in a new light", Genes & Development 17: 545-580 2003, Cold Spring Harbor Laboratory Press.
Welling et al., "Radiochemical and biological characteristics of 99m-Tc-UBI 29-41 for imaging of bacterial infections", Nuclear Medicine and Biology 29 (2002) 413-422.
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
U.S. Appl. No. 13/783,007, filed Mar. 1, 2013, Savage.
U.S. Appl. No. 14/694,028, filed Apr. 23, 2015, Beus et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/750,928, filed Jun. 25, 2015, Genberg et al.
U.S. Appl. No. 14/873,013, filed Oct. 1, 2015, Savage et al.
U.S. Appl. No. 14/926,738, filed Oct. 29, 2015, Vazquez et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.
Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Clara et al., "Preclinical evaluation of magainin-A as a contraceptive antimicrobial agent", Fertility and Sterility 81 (5), pp. 1357-1365, 2004.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl file/o10062704 sl.pdf.
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2014/034986 dated Aug. 28, 2014.
International Search Report for PCT Application No. PCT/US2013/065510 dated Apr. 30, 2015.

(56) References Cited

OTHER PUBLICATIONS

International Search Report for PCT Application No. PCT/US2015/020166 dated Sep. 2, 2015.
International Search Report for PCT Application No. PCT/US2015/038029 dated Sep. 29, 2015.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
Savage et al, "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
BASF, Pluronic® Block Copolymer NF Grades (Poloxamer NF Grades), Technical Bulletive (2004).
Belikov V.G., Pharameutical Chemistry, M., Higher School, 1993, p. 43-47.
Bush, "Staphylococcal Infections", Merck Manuals Professional Edition, http://www.merckmanuals.com/professional/infectious-diseases/gram-positive-cocci/staphylococcal-infections.
Cipolla et al., "Inhaled antibiotics to treat lung infection", Pharm Pat Anal., Sep. 2013.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961.
Food definition, Merriam Webster, https://www.merriam-webster.com/ dictionary/food, Accessed Feb. 12, 2018.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
Jones et al, "Physicochemical Characterization of Hexetidine-Impregnated Endotracheal Tube Poly (Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-676, 1954.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, Co-Published Dec. 20, 2007).
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.
U.S. Appl. No. 15/934,534, filed Mar. 23, 2018, Savage.
U.S. Appl. No. 15/895,848, filed Feb. 13, 2018, Genberg, et al.
U.S. Appl. No. 15/926,534, filed Mar. 20, 2018, Savage.
U.S. Appl. No. 15/926,577, filed Mar. 20, 2018, Savage et al.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.

\* cited by examiner

CATIONIC STEROIDAL ANTIMICROBIAL PRODRUG COMPOSITIONS AND USES THEREOF

CROSS-REFERENCE TO RELATED APPLICATIONS

This application claims the benefit of U.S. Provisional Application No. 62/061,087, filed Oct. 7, 2014, and also U.S. Provisional Application No. 62/192,221, filed Jul. 14, 2015, the disclosures of which are incorporated herein in their entirety.

BACKGROUND

1. Field of Invention

The disclosure relates generally to cationic steroidal antimicrobial ("CSA") compounds and CSA prodrug compounds.

2. Relevant Technology

Cationic steroidal anti-microbial (CSA) compounds, sometimes referred to as ceragenin compounds, can include synthetically produced, small molecule chemical compounds that include a sterol or steroid backbone having various charged groups (e.g., amino, guanidino, and other cationic groups) attached to the backbone. The compounds mimic the three-dimensional structure of naturally occurring anti-microbial peptides and have shown promise as antimicrobial agents. In certain circumstances, it may be desired to provide greater stability, altered solubility, or reduced or delayed chemical reactivity of the compounds.

BRIEF SUMMARY

Embodiments of the present disclosure include CSA prodrug compositions, including pharmaceutically acceptable salts, stereoisomers, solvates, or polymorphs thereof, comprising a pharmaceutically and/or diagnostically active CSA compound or a pharmaceutically acceptable salt, stereoisomer, solvate, or polymorph thereof, and one or more cleavable groups. Certain embodiments include CSA compounds prepared in an inactive form and capable of conversion to an active form (e.g., by removal of the one or more cleavable groups) upon administration to a subject, upon preparation of a pharmaceutical formulation containing the CSA compound, and/or upon exposure to physiological conditions. Additionally, the present application describes pharmaceutical compositions comprising said prodrug or a pharmaceutically acceptable salt, stereoisomer, solvate, or polymorph thereof and one or more pharmaceutically acceptable excipients. Finally, the present application describes methods of treatment of infections in a patient in need utilizing the prodrugs, or pharmaceutically acceptable salts, stereoisomers, solvates, or polymorphs thereof and/or the pharmaceutical compositions described herein.

The prodrugs of the present application generally include a CSA compound or a pharmaceutically acceptable salt, stereoisomer, solvate, or polymorph thereof (A) and one or more cleavable groups (B) directly bound to the CSA compound according to formula I:

$$A-B_n \qquad (I)$$

wherein n is an integer.

By way of example and in some embodiments, exemplary CSA's according to (A) can be compounds or pharmaceutically acceptable salts or stereoisomers or solvates or polymorphs having the general formula II:

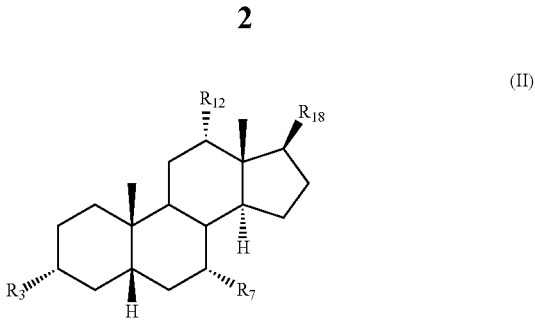

wherein, $R_3$, $R_7$, $R_{12}$ and $R_{18}$ are described herein.

The one or more cleavable groups (B) include protecting groups (e.g., amino protecting groups) that cleave from the CSA compound under physiological conditions and/or during the preparation of a pharmaceutical formulation.

In some embodiments, the charged cationic functional groups of the CSA compounds described herein may be reversibly converted to an inactive or less than fully active form. In particular embodiments, CSA compounds are prepared in an inactive or less active form as prodrugs, such that when administered to a subject (e.g., animal or human) in an inactive or less active form, the CSA prodrug compound is converted to an active form through normal metabolic processes of the subject or by physiological conditions within the subject. In other embodiments, the CSA prodrug compounds exhibit an inactive or less active form capable of conversion to an active form before administration to a subject, such as when the CSA prodrug compound is added to a pharmaceutical formulation or otherwise associated with other compounds during the preparation of a pharmaceutical formulation.

Embodiments of CSA prodrugs may be useful for altering a CSA composition to achieve pharmaceutical advantages and benefits. For example, a CSA prodrug may offer benefits, advantages, and uses not available in a fully active CSA compound, such as altered solubility, lipophilicity, ionization activity, diffusion mechanics, and/or pKa values (e.g., with respect to an amino or gaunidino cationic functional group). A CSA prodrug might be used to improve how a medicine is absorbed, distributed, metabolized, and/or excreted, and may widen the therapeutic window, increase the half-life in serum, and/or maintain concentrations above effective dose for sufficient duration to be effective.

Other aspects and advantages of the invention will be apparent from the following description and the appended claims. The various characteristics described above, as well as other features, will be readily apparent to those skilled in the art upon reading the following description. This summary is therefore not intended to identify key or essential features of the claimed subject matter, nor is it intended to be used as an aid in limiting the scope of the claims.

DETAILED DESCRIPTION

Figure 1:
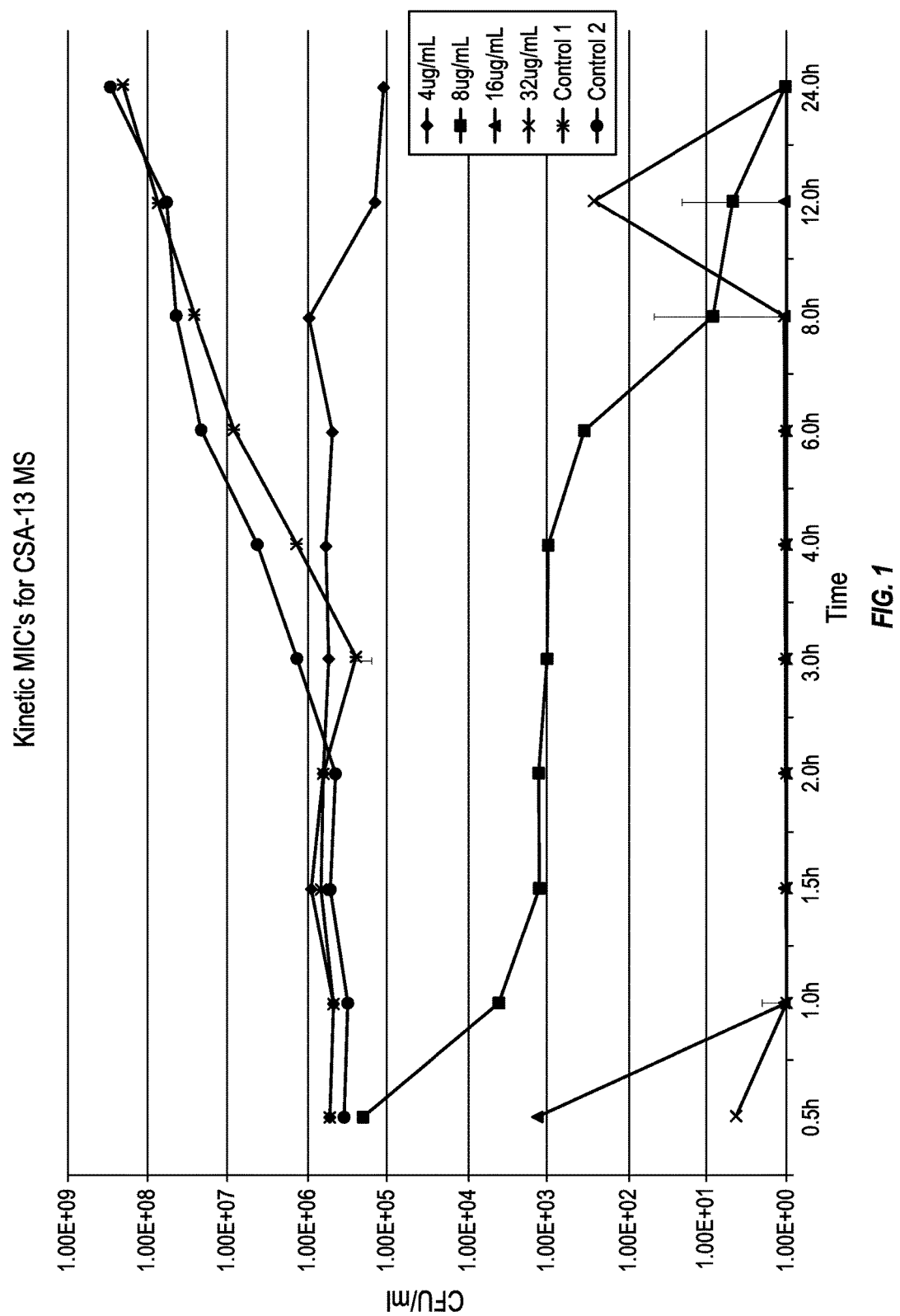
FIG. 1 is a chart that graphically illustrates Kinetic Minimum Inhibitory Concentrations of Cationic Steroidal Antimicrobial prodrug CSA-13 MS (illustrated as colony forming units per milliliter versus time).

The following is directed to various embodiments of the disclosure. The embodiments disclosed should not be interpreted, or otherwise used, to limit the scope of the disclosure including the claims. In addition, those having ordinary skill in the art will appreciate that the following description has broad application, and the discussion of any embodiment is not intended to suggest that the scope of the disclosure, including the claims, is limited to that embodiment.

Disclosed herein are prodrugs or pharmaceutically acceptable salts, or stereoisomers, or solvates or polymorphs thereof comprising a pharmaceutically and/or diagnostically active cationic steroidal antimicrobial (hereinafter "CSA") compound or a pharmaceutically acceptable salt, or a stereoisomer, or a solvate or a polymorph thereof, and one or more cleavable groups. Additionally, the present application describes pharmaceutical compositions comprising said prodrug or a pharmaceutically acceptable salt, or a stereoisomer, or a solvate or a polymorph thereof and one or more pharmaceutically acceptable excipients. Finally, the present application describes methods of treatment of bacterial infections in a patient in need utilizing the prodrugs or pharmaceutically acceptable salts, or stereoisomers, or solvates or polymorphs thereof and/or the pharmaceutical compositions described herein.

The term "prodrug" as employed herein is a medication or compound that is administered or used in an inactive or less than fully active form, and is then converted to its active form through a normal metabolic or chemical process, such as hydrolysis of an ester form of the drug. A "prodrug" is a precursor chemical compound of a drug. Instead of administering a drug, a prodrug might be used instead to improve how a medicine is absorbed, distributed, metabolized, and excreted (ADME). Prodrugs are often designed to improve bioavailability when a drug itself is poorly absorbed from the gastrointestinal tract. A prodrug may be used to improve how selectively the drug interacts with cells or processes that are not its intended target. Specifically, the cleavable group(s) may be chosen such that it undergoes a relatively slow hydrolysis to the active form of the drug at normal physiological pH but undergoes hydrolysis at higher rates when the pH is either more basic or more acidic.

Without wishing to be bound by any particular theory, the prodrugs described herein, non-limiting examples of which include methane sulfonate derivatives of CSA-13 (CSA-13 MS), when exposed to body fluids (or aqueous solutions), undergo a slow hydrolysis that leads to conversion of the pro-drug form to the active form of the drug. This conversion can be selected to occur at higher rates when the pH is either more basic or more acidic than neutral pH. The prodrug form of CSA-13 may preferentially undergo hydrolysis at such sites leading to increased concentration at the site(s) of interest. Furthermore, the prodrugs described herein may confer the following advantages: (i) widen the therapeutic window; (ii) increase half-life in serum; and/or (iii) maintain concentrations above effective dose for sufficient duration to be effective.

A more generalized embodiment the present invention provides for prodrugs or pharmaceutically acceptable salts, or stereoisomers, or solvates or polymorphs thereof, comprising CSA compounds and one or more cleavable groups according to formula I $$A\text{-}B_n \quad (I)$$

wherein, A is a CSA compound or a pharmaceutically acceptable salt, or a stereoisomer, or a solvate or a polymorph thereof; B is one or more cleavable groups directly bound to the CSA compound; and n is an integer selected from the group consisting of 1, 2, 3 and 4.

Definitions

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, cyano, mercapto, alkylthio, heterocyclyl, aryl, heteroaryl, carboxyl, carbalkoyl, carboxamido, carbonyl, carbamyl, ureayl, guanidinyl, alkyl, alkenyl, alkynyl, nitro, amino, alkoxyl, aryloxyl, heteroaryloxyl, amido, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, mercapto, and alkylthio.

Unless otherwise indicated, the term "alkynyl" as used herein by itself or as part of another group refers to straight or branched chain radicals of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, mercapto, and alkylthio.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the rings and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

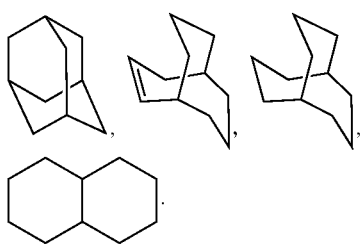

Further, any cycloalkyl may be optionally substituted through any available carbon atoms with one or more groups selected from the group consisting of hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, mercapto, and alkylthio.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl, 1-naphthyl and 2-naphthyl) and may optionally include one to three additional carbocyclic or heterocyclic fused rings, for example

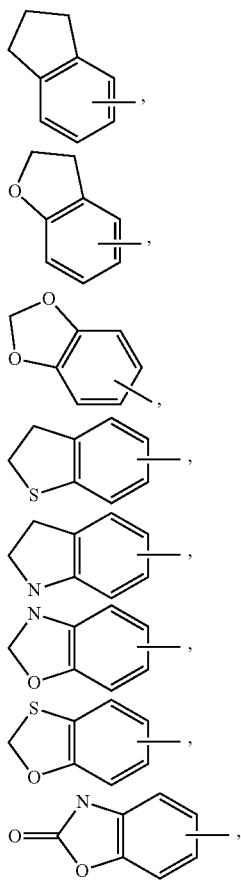

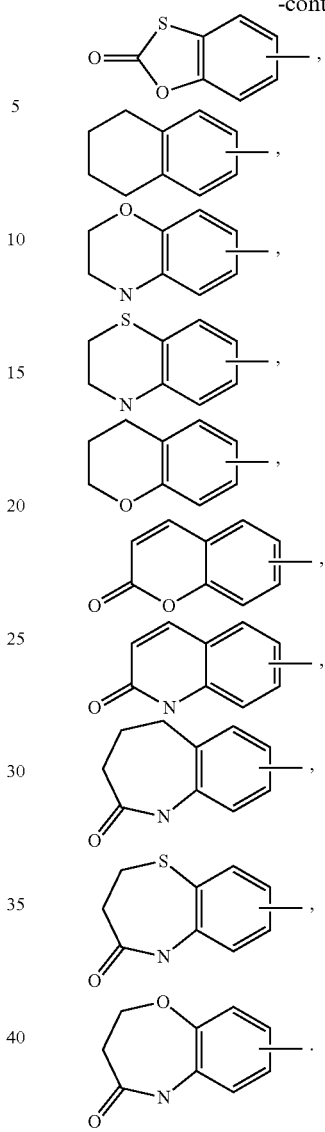

Further, "aryl" as defined herein, may optionally be substituted with one or more functional groups, such as halo, alkyl, alkenyl, alkynyl, cycloalkyl, cycloalkylalkyl, heterocyclyl, heterocycloalkyl, aryl, heteroaryl, arylalkyl, arylalkenyl, heteroarylalkyl, heteroarylalkenyl, haloalkyl, $CF_3$, hydroxy, alkoxy, haloalkoxy, $OCF_3$, $OCF_2H$, aryloxy, heteroaryloxy, arylalkoxy, alkylcarbonyloxy, arylcarbonyloxy, aryloxyalkyl, alkylcarbonyl, arylcarbonyl, alkoxycarbonyl, aminocarbonyl, alkylaminocarbonyl, arylaminocarbonyl, aminocarbonylaryl, heteroarylheteroaryl, nitro, cyano, arylazo, amino, substituted amino wherein the amino includes 1 or 2 substituents (which are alkyl or aryl), alkylcarbonylamino, arylcarbonylamino, alkylsulfonylamino, arylsulfonylamino, mercapto, alkylthio, arylthio, alkoxyarylthio, heteroarylthio, arylsulfinyl, alkylsulfonyl, arylsulfonyl, arylthioalkyl, arylsulfinylalkyl, arylsulfonylalkyl, alkylsulfonylalkyl, or arylsulfonaminocarbonyl.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur. Such rings may be fused to an aryl, cycloalkyl, heteroaryl or heterocyclyl group and include possible N-oxides as described in Katritzky, A. R. and Rees, C. W., eds. Comprehensive Heterocyclic Chemistry: The Structure, Reactions, Synthesis and Uses of Heterocyclic Compounds 1984, Pergamon Press, New York, N.Y.; and Katritzky, A. R., Rees, C. W., Scriven, E. F., eds. Comprehensive Heterocyclic Chemistry II: A Review of the Literature 1982-1995 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

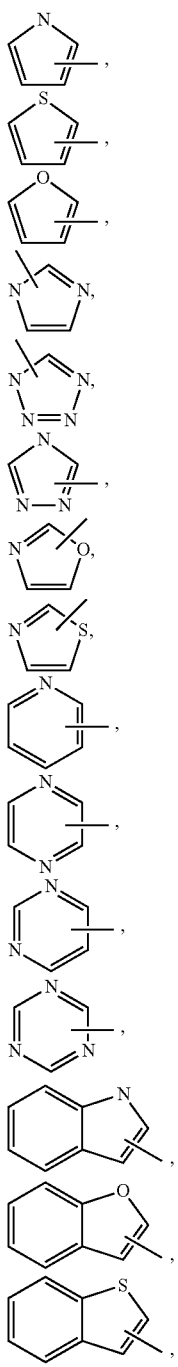

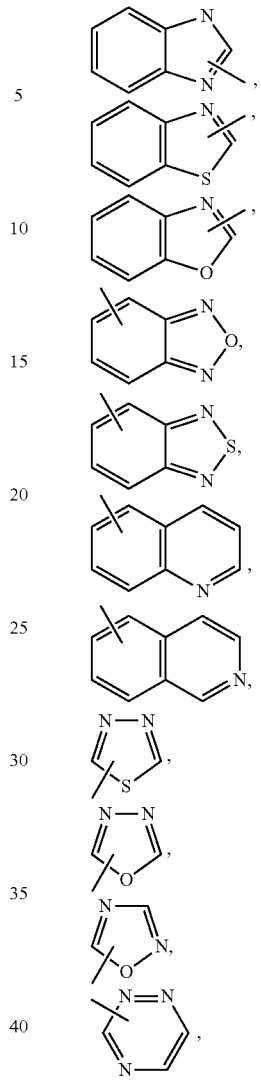

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable, 4 to 7-membered monocyclic ring system which may be saturated or unsaturated, and which consists of carbon atoms, with one to four heteroatoms selected from the group consisting of nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. Comprehensive Heterocyclic Chemistry: The Structure, Reactions, Synthesis and Uses of Heterocyclic Compounds 1984, Pergamon Press, New York, N.Y.; and Katritzky, A. R., Rees, C. W., Scriven, E. F., eds. Comprehensive Heterocyclic Chemistry II: A Review of the Literature 1982-1995 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups, respectively, as defined above having an aryl substituent as defined above. Representative examples of arylalkyl include, but are not limited to, benzyl, 2-phenylethyl, 3-phenylpropyl, benzhydryl and naphthylmethyl and the like.

The terms "alkoxy", "aryloxy", "heteroaryloxy", "arylalkyloxy" or "heteroarylalkyloxy" as employed herein alone or as part of another group include, respectively, alkyl, aryl, heteroaryl, arylalkyl and heteroarylalkyl groups as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein alone or as part of another group, refers to a —CN group.

The term "methylene," as used herein alone or as part of another group, refers to a —$CH_2$— group.

The term "nitro," as used herein alone or as part of another group, refers to a —$NO_2$ group.

The term "acyl", as employed herein alone or as part of another group includes, alkyl, aryl, heteroaryl, arylalkyl and heteroarylalkyl groups as defined above linked through a carbonyl group.

The term "amino", as employed herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, alkylaminocarbonylalkyl, and alkylamidoalkyl.

CSA Molecules and Compositions

Cationic steroidal anti-microbial (CSA) molecules, sometimes referred to as CSA compounds or ceragenin compounds, can include synthetically produced, small molecule chemical compounds that include a sterol or steroid backbone having various charged groups (e.g., amino, guanidino, and other cationic groups) attached to the backbone. The compounds mimic the three-dimensional structure of naturally occurring anti-microbial peptides. CSAs are cationic and amphiphilic, based upon the functional groups attached to the backbone. The backbone can be used to orient cationic functional groups, such as amino or guanidino groups, on a face or plane of the backbone. They may be facially amphiphilic with a hydrophobic face and a polycationic face.

Without wishing to be bound by theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the outer cellular membrane of bacteria and other microbes and inserting into the cell membrane forming a pore that allows the leakage of ions that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the outer membrane of the bacteria.

Examples of CSA compounds according to (A) of Formula I are shown in Formulae II, III and IV, wherein Formula IV differs from Formula III by omitting $R_{15}$ and the ring carbon to which it is attached. Formula II is a special example of Formulae III and IV. The R groups shown in the Formulae can have a variety of different structures, as discussed below.

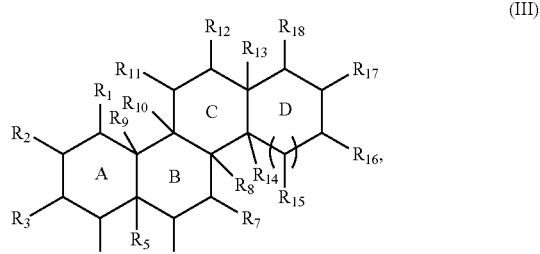

(III)

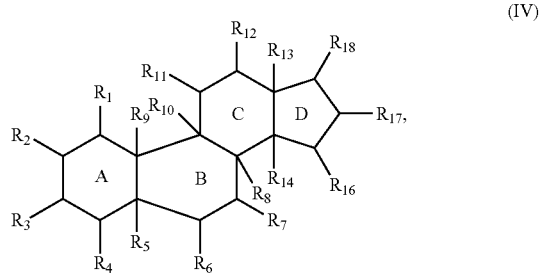

(IV)

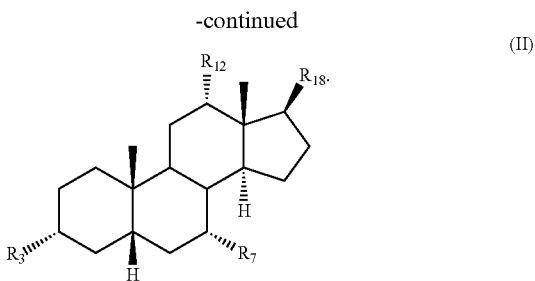

(II)

CSA compounds having a variety of different residues (R groups) and methods of manufacturing CSA compounds useful in accordance with the present disclosure are disclosed in U.S. Pat. Nos. 6,350,738, 6,486,148, 6,767,904, 7,598,234 and 7,754,705, and U.S. Application Nos. 14/866,213, 14/341,304, 62/191,916, 62/191,922, and 62/191,926 which are incorporated herein by reference.

In embodiments of Formulas III and IV, each of fused rings A, B, C, and D may be independently saturated, or may be fully or partially unsaturated, provided that at least two of A, B, C, and D are saturated, wherein rings A, B, C, and D form a ring system. Other ring systems can also be used, e.g., 5-member fused rings and/or compounds with backbones having a combination of 5- and 6-membered rings.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid molecule, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl) aminoalkyl, $H_2N$—$HC(Q_5)$-$C(O)$—$O$—, $H_2N$—$HC(Q_5)$-$C(O)$—$N(H)$—, a substituted or unsubstituted azidoalkyloxy, a substituted or unsubstituted cyanoalkyloxy, P.G.-HN—HC(Q$_5$)-C(O)—O—, a substituted or unsubstituted guanidinoalkyloxy, a substituted or unsubstituted quaternary ammonium alkylcarboxy, and a substituted or unsubstituted guanidinoalkyl carboxy, where $Q_5$ is a side chain of any amino acid (including a side chain of glycine, i.e., H), and P.G. is an amino protecting group.

In some embodiments, $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl) aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—HC(Q$_5$)-C(O)—O—, guanidinoalkyloxy, and guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a quaternary ammonium alkylcarboxy, a substituted or unsubstituted di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—HC(Q$_5$)-C(O)—O—, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$, preferably at least two, are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino-($C_1$-$C_{22}$) alkylamino, a substituted or unsubstituted ($C_1$-$C_{22}$) aminoalkyl, a substituted or unsubstituted aryl, a substituted or unsubstituted arylamino-($C_1$-$C_{22}$) alkyl, a substituted or unsubstituted ($C_1$-$C_{22}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkyloxy-($C_1$-$C_{22}$) alkyl, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted ($C_1$-$C_{22}$) aminoalkylcarboxamido, a substituted or unsubstituted di($C_1$-$C_{22}$ alkyl) aminoalkyl, $H_2N$—$HC(Q_5)$-$C(O)$—$O$—, $H_2N$—$HC(Q_5)$-$C(O)$—$N(H)$—, a substituted or unsubstituted ($C_1$-$C_{22}$) azidoalkyloxy, a substituted or unsubstituted ($C_1$-$C_{22}$) cyanoalkyloxy, P.G.-HN—HC(Q$_5$)-C(O)—O—, a substituted or unsubstituted ($C_1$-$C_{22}$) guanidinoalkyloxy, a substituted or unsubstituted ($C_1$-$C_{22}$) quaternary ammonium alkylcarboxy, and a substituted or unsubstituted ($C_1$-$C_{22}$) guanidinoalkyl carboxy, where $Q_5$ is a side chain of any amino acid (including a side chain of glycine, i.e., H), and P.G. is an amino protecting group;

In some embodiments, $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$)

alkyl, a substituted or unsubstituted ($C_1$-$C_{22}$) aminoalkyl, a substituted or unsubstituted aryl, a substituted or unsubstituted ($C_1$-$C_{22}$) haloalkyl, a substituted or unsubstituted ($C_2$-$C_6$) alkenyl, a substituted or unsubstituted ($C_2$-$C_6$) alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted di($C_1$-$C_{22}$) alkyl) aminoalkyl, $H_2N-HC(Q_5)-C(O)-O-$, $H_2N-HC(Q_5)-C(O)-N(H)-$, a substituted or unsubstituted ($C_1$-$C_{22}$) azidoalkyloxy, a substituted or unsubstituted ($C_1$-$C_{22}$) cyanoalkyloxy, $P.G.-HN-HC(Q_5)-C(O)-O-$, a substituted or unsubstituted ($C_1$-$C_{18}$) guanidinoalkyloxy, and ($C_1$-$C_{22}$) guanidinoalkylcarboxy, where $Q_5$ is a side chain of any amino acid, and P.G. is an amino protecting group.

In the embodiments, at least two of $R_3$, $R_7$, and $R_{12}$ may independently include a cationic moiety (e.g., amino or guanidino groups) bonded to the steroid backbone structure via a non-hydrolysable or hydrolysable linkage. For the embodiments of the present disclosure, the linkage is preferably non-hydrolysable under conditions of sterilization and storage, and physiological conditions. Such cationic functional groups (e.g., amino or guanidino groups) may be separated from the backbone by at least one, two, three, four or more atoms.

Optionally, a tail moiety may be attached to the backbone structures at $R_{18}$. The tail moiety may have variable chain length or size and may be charged, uncharged, polar, nonpolar, hydrophobic, amphipathic, and the like. The tail moiety may, for example, be configured to alter the hydrophobicity/hydrophilicity of the ceragenin compound. CSA compounds of the present disclosure having different degrees of hydrophobicity/hydrophilicity may, for example, have different rates of uptake into different target microbes.

In some embodiments, the CSA compound is according to Formula II.

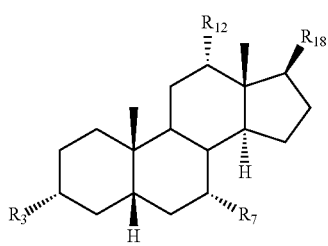

(II)

where, $R_3$ is selected from the group consisting of: hydroxy, optionally substituted ($C_1$-$C_{18}$) alkoxy, optionally substituted amino, optionally substituted ($C_1$-$C_{18}$) alkylamido, optionally substituted ($C_1$-$C_{18}$) alkylureayl, optionally substituted ($C_1$-$C_{18}$) alkylcarboxy, and optionally substituted ureayl;

$R_7$ is selected from the group consisting of: H, hydroxy, optionally substituted ($C_1$-$C_{18}$) alkoxy, optionally substituted amino, optionally substituted ($C_1$-$C_{18}$) alkylamido, optionally substituted ($C_1$-$C_{18}$) alkylureayl and optionally substituted ($C_1$-$C_{18}$) alkylcarboxy;

$R_{12}$ is selected from the group consisting of: H, hydroxy, optionally substituted ($C_1$-$C_{18}$) alkoxy, optionally substituted amino, optionally substituted ($C_1$-$C_{18}$) alkylamido, optionally substituted ($C_1$-$C_{18}$) alkylureayl, optionally substituted ($C_1$-$C_{18}$) alkylcarboxy, and optionally substituted ureayl; and $R_{18}$ is selected from the group consisting of: H and optionally substituted ($C_1$-$C_{18}$) alkyl.

In some embodiments, at least $R_{18}$ has the following structure:

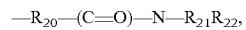

$-R_{20}-(C=O)-N-R_{21}R_{22}$, where, $R_{20}$ is omitted or substituted or unsubstituted alkyl, alkenyl, alkynyl, or aryl, such as substituted or unsubstituted $C_1$-$C_{10}$ alkyl, substituted or unsubstituted $C_1$-$C_{10}$ alkenyl, substituted or unsubstituted $C_1$-$C_{10}$ alkynyl, or substituted or unsubstituted $C_6$ or $C_{10}$ aryl, and $R_{21}$ and $R_{22}$ are independently selected from the group consisting of hydrogen, substituted or unsubstituted alkyl, substituted or unsubstituted alkenyl, substituted or unsubstituted alkynyl, or substituted or unsubstituted aryl, provided that at least one of $R_{21}$ and $R_{22}$ is not hydrogen.

In some embodiments, $R_{21}$ and $R_{22}$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_7$-$C_{13}$ aralkyl, optionally substituted (5 to 10 membered heteroaryl)-$C_1$-$C_6$ alkyl, optionally substituted $C_3$-$C_{10}$ carbocyclyl, optionally substituted $C_4$-$C_{10}$ (carbocyclyl)alkyl, optionally substituted (5 to 10 membered heterocyclyl)-$C_1$-$C_6$ alkyl, optionally substituted amido, and a suitable amine protecting group, provided that at least one of $R_{21}$ and $R_{22}$ is not hydrogen.

In some embodiments, $R_{21}$ and $R_{22}$, together with the atoms to which they are attached, can form an optionally substituted 5 to 10 membered heterocyclyl ring.

In certain embodiments, the CSA compound or pharmaceutically acceptable salt, or stereoisomer, or solvate or polymorph (A) has a CSA structure selected from the group consisting of:

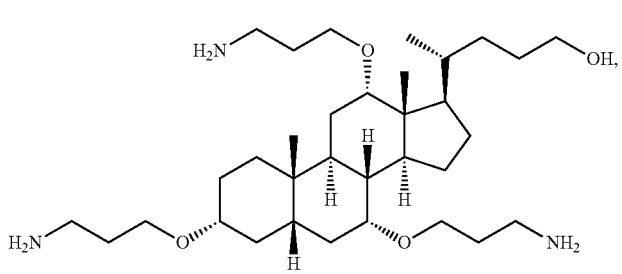

(CSA-8)

-continued
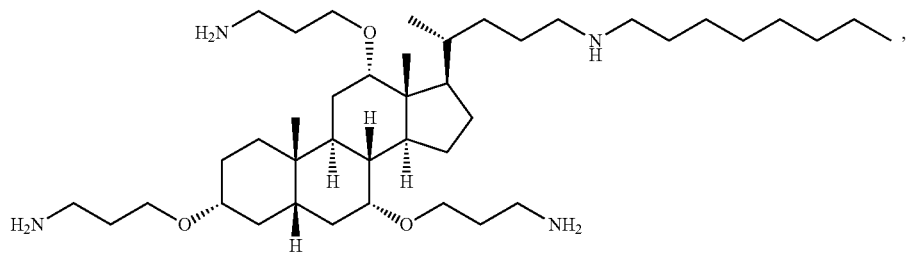
(CSA-13)
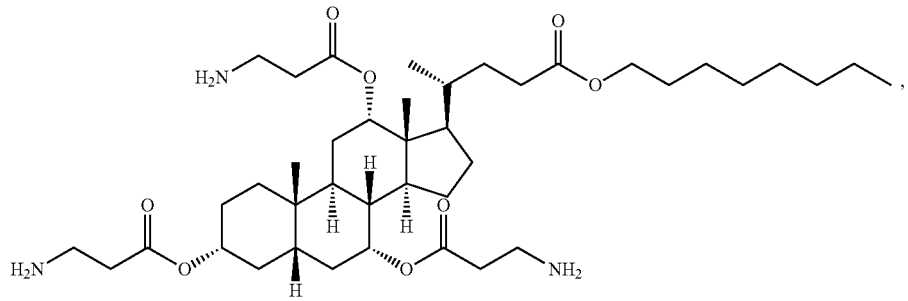
(CSA-44)
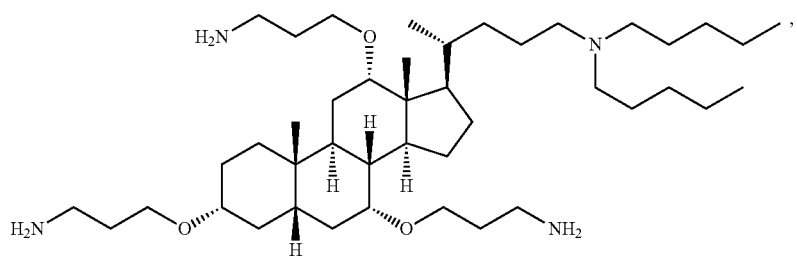
(CSA-90)
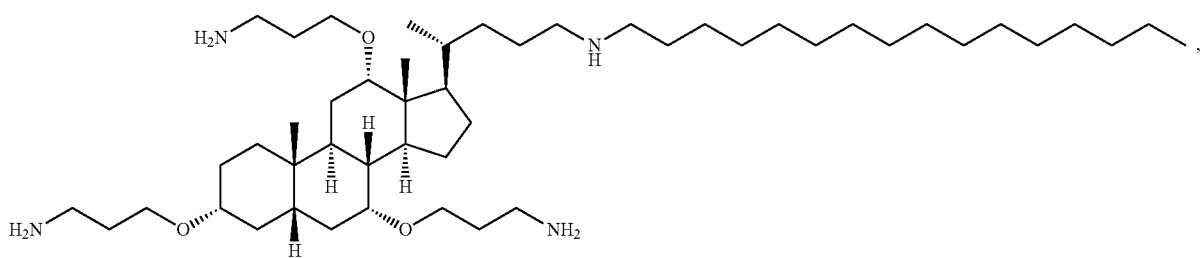
(CSA-92)
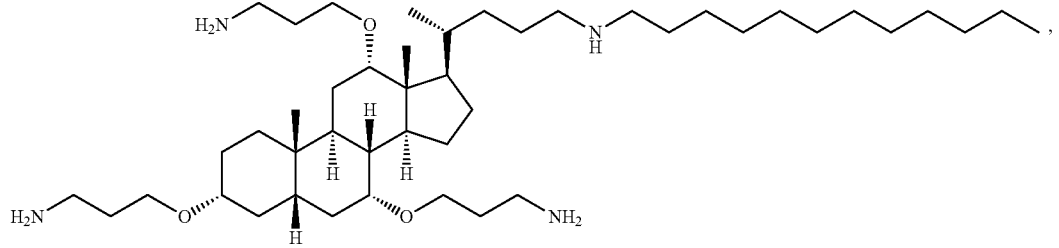
(CSA-131)
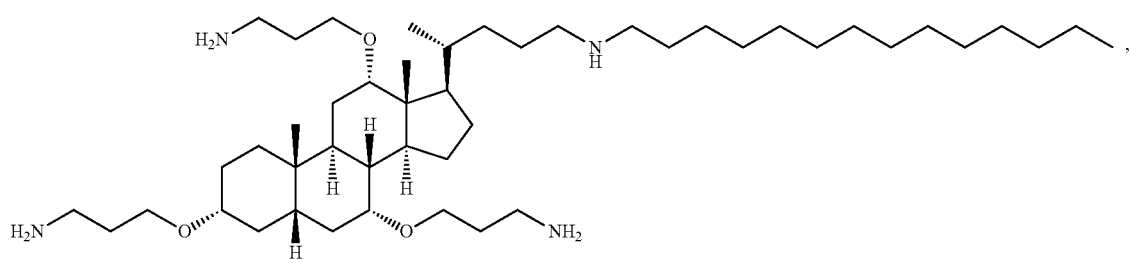
(CSA-134)

(CSA-136)
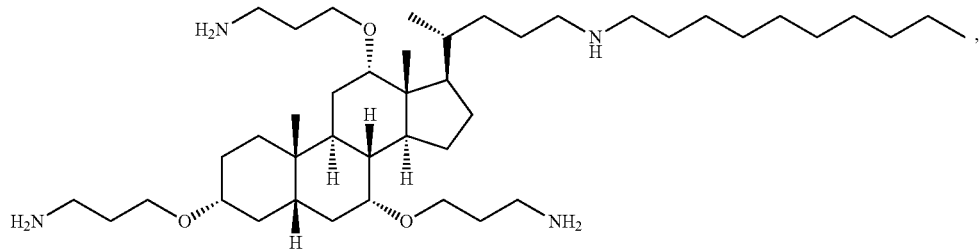
(CSA-137)
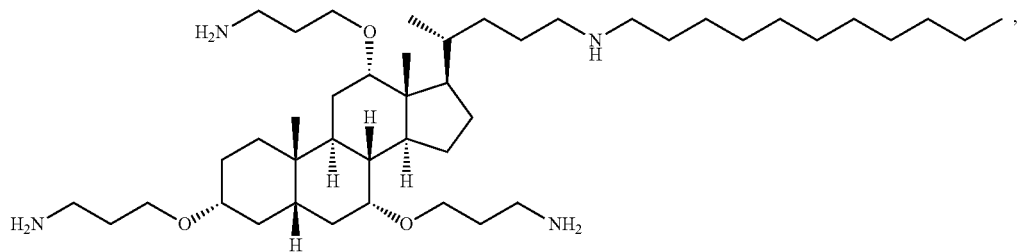
(CSA-138)
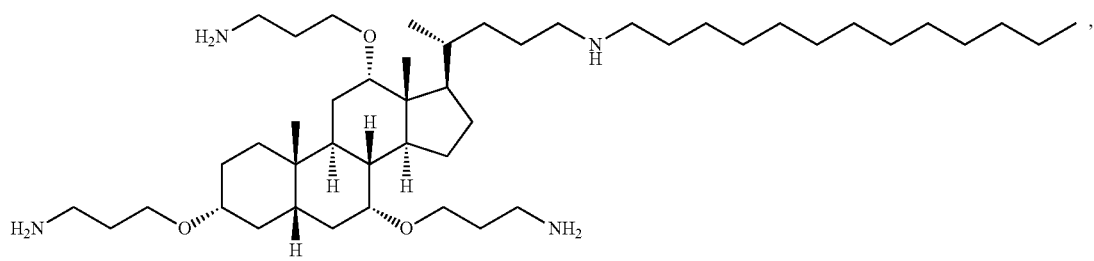
(CSA-142)
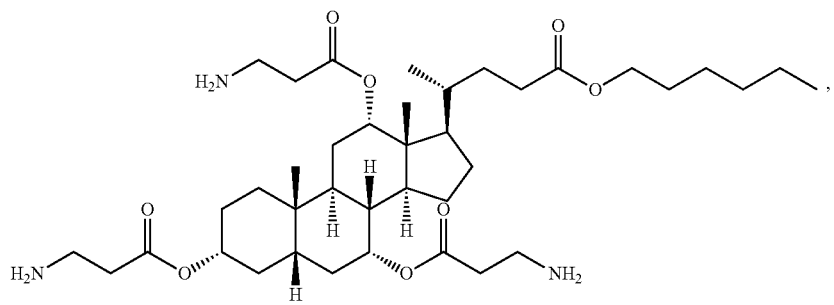
(CSA-144)
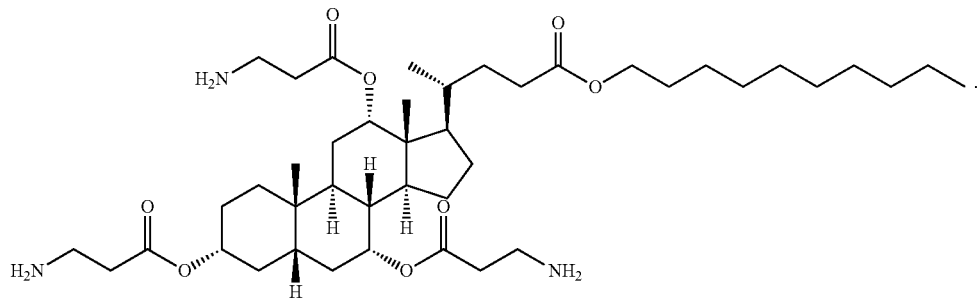

-continued
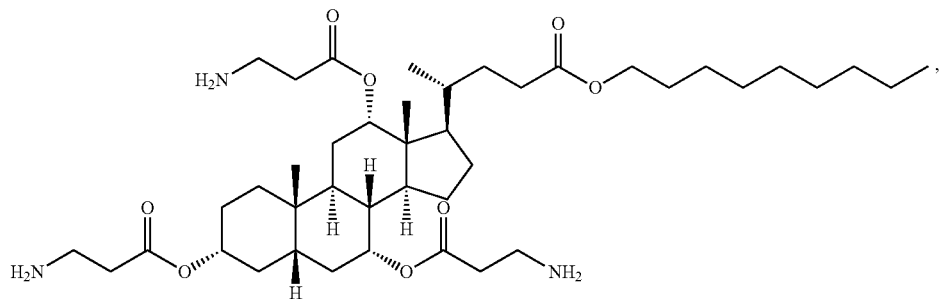
(CSA-145)
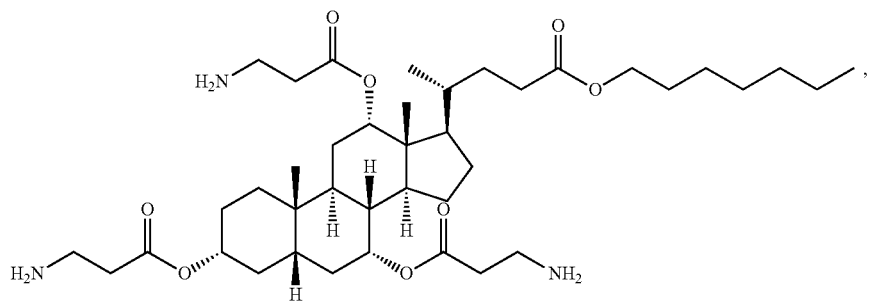
(CSA-146)
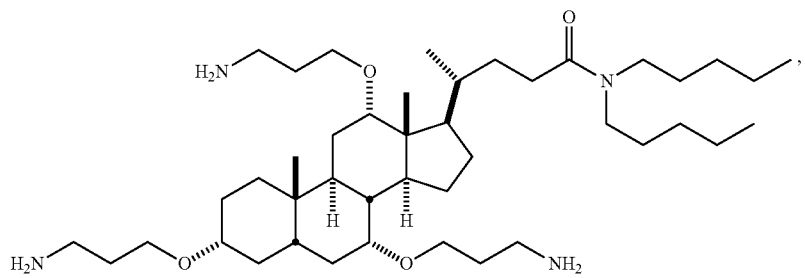
(CSA-190)
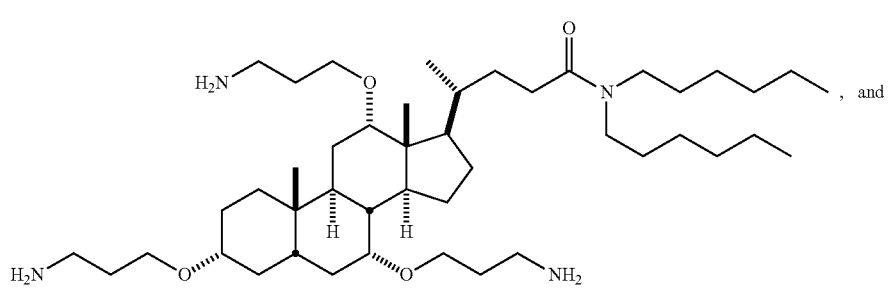
(CSA)-191, and
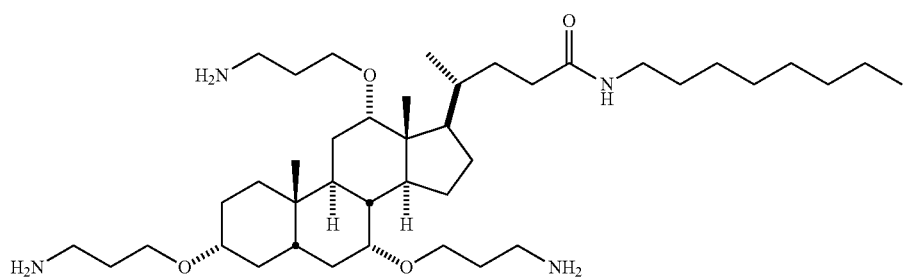
(CSA-192)
In some embodiments, the CSA compound or pharmaceutically acceptable salt, or stereoisomer, or solvate or polymorph (A) has the CSA structure CSA-13 with the following chemical structure:

In some embodiments, the CSA compound or pharmaceutically acceptable salt, or stereoisomer, or solvate or polymorph (A) has the CSA structure CSA-192 with the following chemical structure:

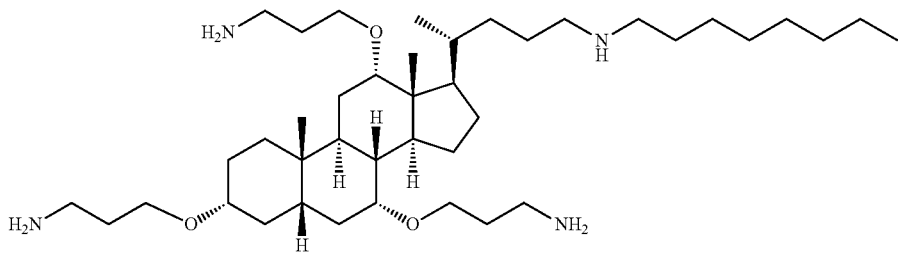

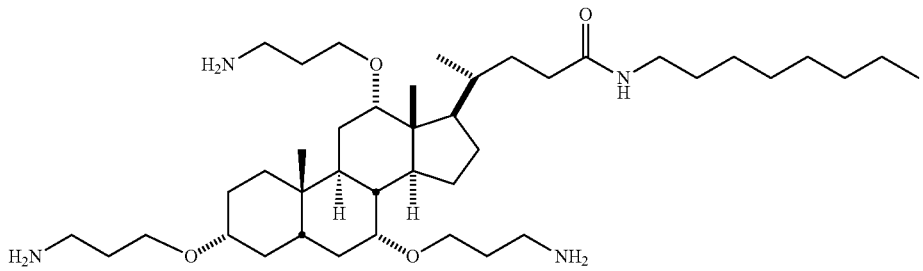

As discussed herein, the anti-microbial activity of the CSA compounds can be affected by the orientation of the substituents attached to the backbone structure. In one embodiment, the substituents attached to the backbone structure are oriented on a single face of the CSA compound. Accordingly, each of $R_3$, $R_7$, and $R_{12}$ may be positioned on a single face of the steroid backbone embodiments shown in Formulas II, III, and IV. In addition, $R_{18}$ may be positioned on the same single face.

In some embodiments, one or more of $R_3$, $R_7$, or $R_{12}$ may include an amino group as a cationic functional group and may be bonded to the steroid backbone by an ether linkage. For example, one or more of $R_3$, $R_7$, or $R_{12}$ may be an aminoalkyloxy group. An example includes $H_2N$-alkyl-O—, wherein the alkyl portion is straight or branched and has from 1 to 25 carbon atoms or more. In particular embodiments, the alkyl portion has from 1 to 15 carbon atoms. In other particular embodiments, the alkyl portion has from 1 to 6 carbon atoms. In a preferred embodiment, the alkyl portion is a straight chain with 3 carbon atoms, and therefore one or more of $R_3$, $R_7$, or $R_{12}$ may be an aminopropyloxy group such as $H_2N$-propyl-O—.

In some embodiments, one or more of $R_3$, $R_7$, or $R_{12}$ may include a guanidine group as a cationic functional group and may be bonded to the steroid backbone by an ether linkage. For example, one or more of $R_3$, $R_7$, and $R_{12}$ may be a guanidinoalkyloxy group. An example includes $H_2N$—C(=NH)—NH-alkyl-O—,

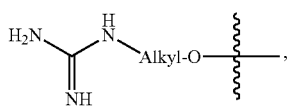

wherein the alkyl portion is defined as with the embodiments described above. In a preferred embodiment, the alkyl portion is a straight chain with 3 carbon atoms, and therefore one or more of $R_3$, $R_7$, or $R_{12}$ may be a guanidinopropyloxy group.

One of skill in the art will recognize that other cationic functional groups may be utilized, and that the cationic functional groups may be bonded to the steroid backbone through a variety of other tethers or linkages. For example, the cationic functional groups may be bonded to the steroid backbone by an ester linkage. For example, one or more of $R_3$, $R_7$, or $R_{12}$ may be an aminoalkylcarboxy or guanidinoalkylcarboxy, such as $H_2N$-alkyl-C(=O)—O— or $H_2N$—C(=NH)—NH-alkyl-C(=O)—O—, wherein the alkyl portion is defined as with the embodiments described above. In other embodiments, the cationic functional groups may be bonded to the steroid backbone by an amide linkage. For example, one or more of $R_3$, $R_7$, or $R_{12}$ may be an aminoalkylcarbonylamino (i.e. aminoalkylcarboxamido) or guanidinoalkylcarbonylamino (i.e. guanidinoalkyl-carboxamido), such as $H_2N$-alkyl-C(=O)—NH— or $H_2N$—C(=NH)—NH-alkyl-C(=O)—NH—, wherein the alkyl portion is defined as with the embodiments described above.

Additionally, one of skill in the art will recognize that the tethers may be of varying lengths. For example, the length between the steroid backbone and the cationic functional group (e.g., amino or guanidino group), may be between 1 and 15 atoms or even more than 15 atoms. In other embodiments, the length may be between 1 and 8 atoms. In a preferred embodiment, the length of the tether is between two and four atoms. In other embodiments, there is no tether, such that the cationic functional group is bonded directly to the steroid backbone.

One of skill in the art will also note that the various cationic functional groups of the present disclosure may be utilized in combination, such that one or more of $R_3$, $R_7$, or $R_{12}$ may include one variation of cationic functional group while one or more of another of $R_3$, $R_7$, or $R_{12}$ of the same compound may include a different variation of cationic functional group. Alternatively, two or more of $R_3$, $R_7$, or $R_{12}$ may include the same cationic functional group, or all of $R_3$, $R_7$, and $R_{12}$ may include the same cationic functional group (in embodiments where all of $R_3$, $R_7$, and $R_{12}$ are cationic functional groups).

Additionally, although in a preferred embodiment one or more cationic functional groups are disposed at $R_3$, $R_7$, or $R_{12}$, one of skill in the art will recognize that in other embodiments, one or more of $R_3$, $R_7$, or $R_{12}$ may not be cationic functional groups and/or one or more cationic functional groups may be disposed at other locations of the steroid backbone. For example, one or more cationic functional groups may be disposed at $R_1$, $R_2$, $R_3$, $R_4$, $R_6$, $R_7$, $R_{11}$, $R_{12}$, $R_{15}$, $R_{16}$, $R_{17}$, and/or $R_{18}$.

CSA Prodrug Compositions

The prodrugs of the present application include a CSA compound or a pharmaceutically acceptable salt, or a stereoisomer, or a solvate or a polymorph thereof (A) and one or more cleavable groups (B) directly bound to the CSA compound according to formula I:

$$A\text{-}B_n \qquad (I)$$

wherein (A) is any of the CSA compounds described above, n is an integer selected from the group consisting of 1, 2, 3 and 4, and the one or more cleavable groups (B) include groups (e.g., amino protecting groups) that cleave from the CSA compound under physiological conditions and/or during the preparation of a pharmaceutical formulation.

In some embodiments, CSA compounds of the present disclosure may be prepared in an inactive or less than fully active form according to the prodrug compound of Formula I. For example, charged cationic functional groups may be reversibly converted to an inactive form by attaching a cleavable group. In particular embodiments, CSA compounds are prepared in an inactive form such that when administered to a subject (e.g., animal or human) in an inactive form, the inactive compound is converted to an active form through normal metabolic processes of the subject or by physiological conditions within the subject.

In other embodiments, the CSA compositions exhibit an inactive form capable of conversion to an active form before administration to a subject, such as when the CSA compositions are added to a pharmaceutical formulation. As used herein, the term "CSA prodrug" describes such CSA compositions exhibiting an inactive form capable of conversion to an active form upon administration to a subject (e.g., through normal metabolic processes and/or upon exposure to physiological conditions) or during preparation of a pharmaceutical formulation.

In certain embodiments, the CSA prodrug or pharmaceutically acceptable salt, or stereoisomer, or solvate or polymorph according to Formula I, II, III, or IV is selected from the group consisting of:

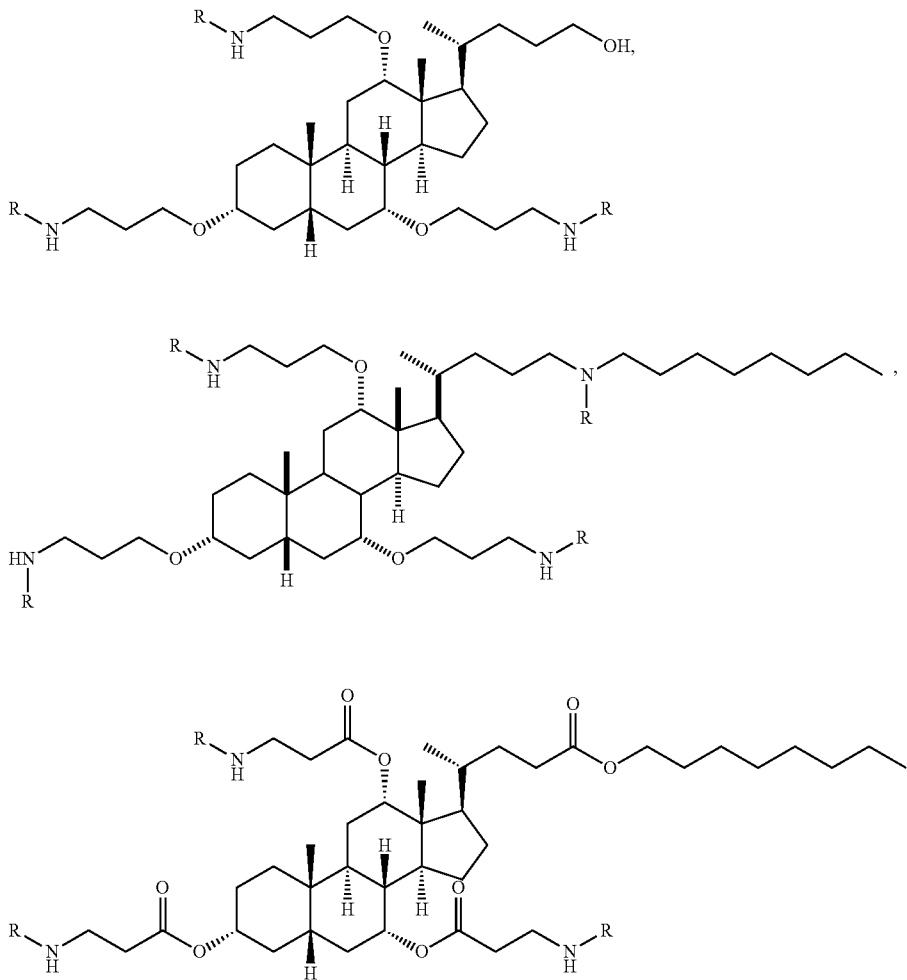

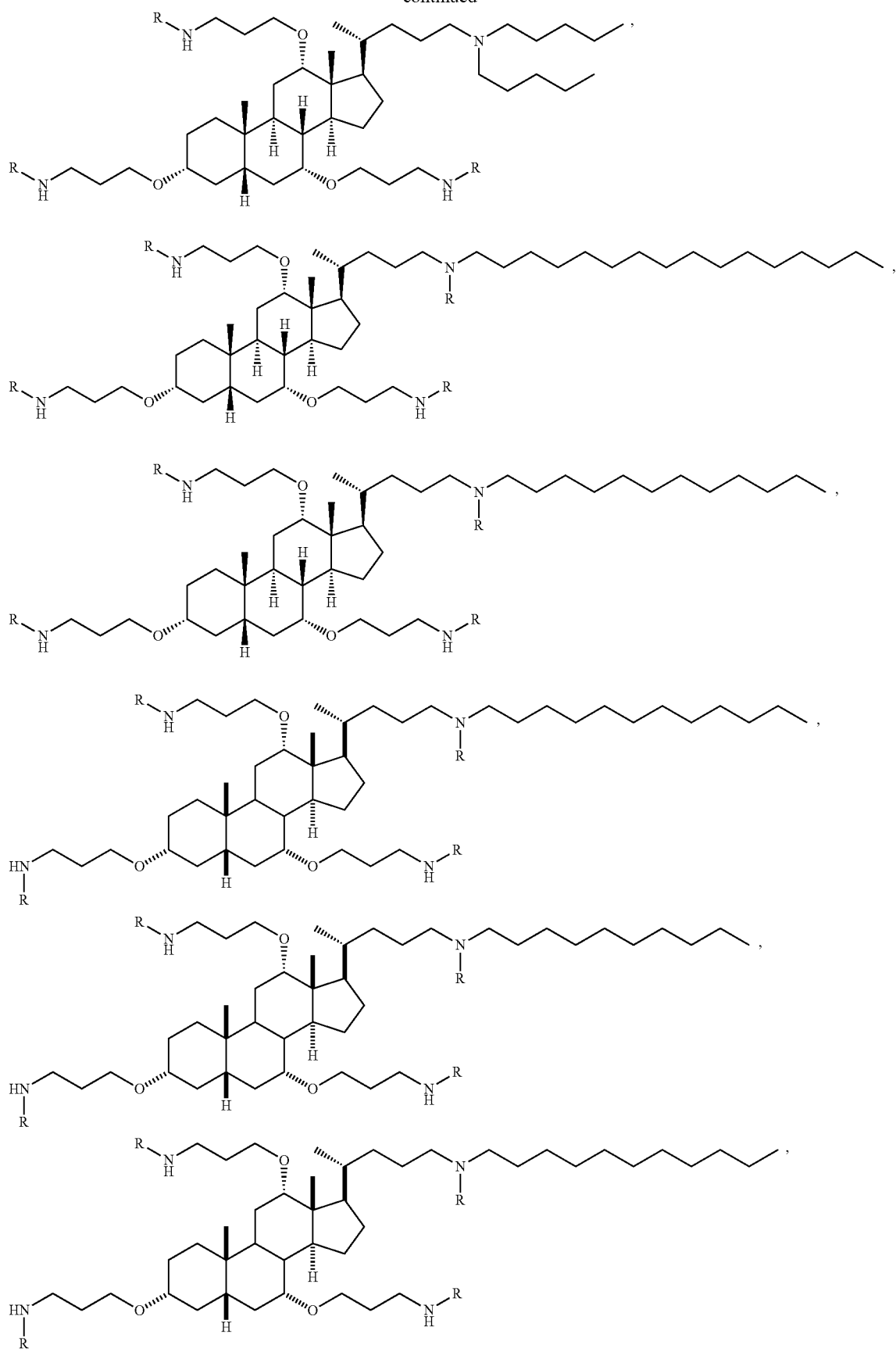

-continued
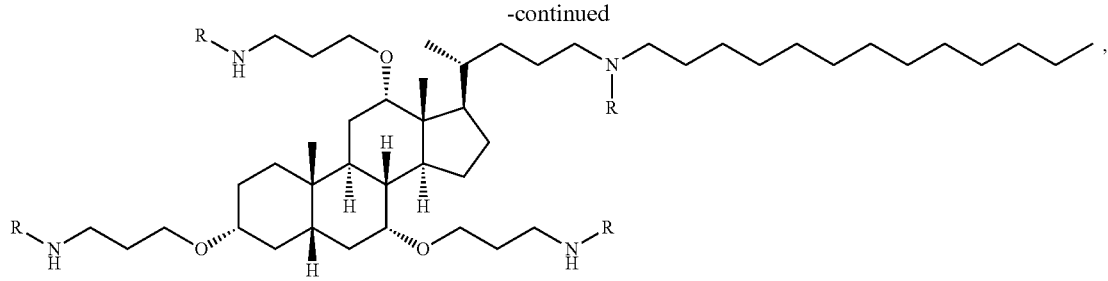
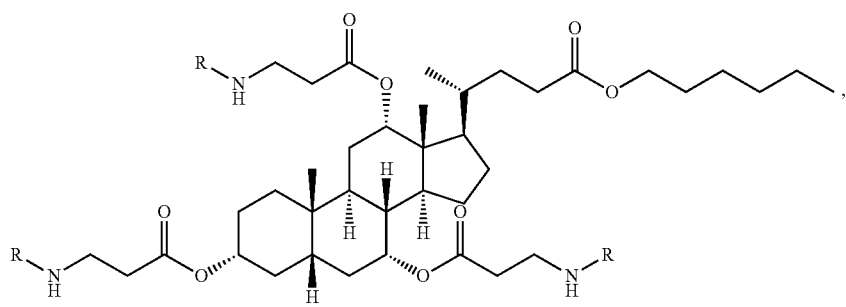
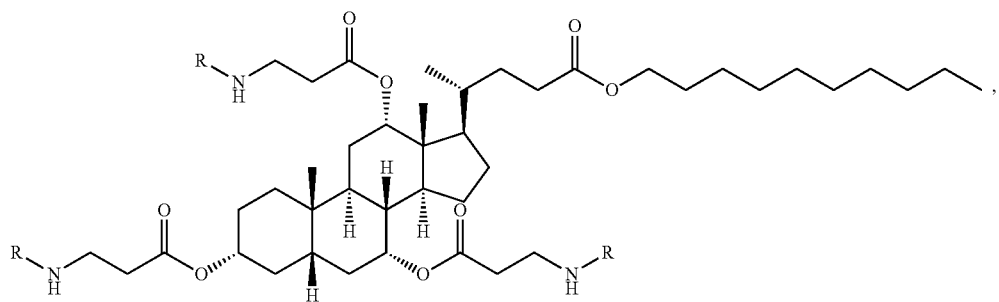
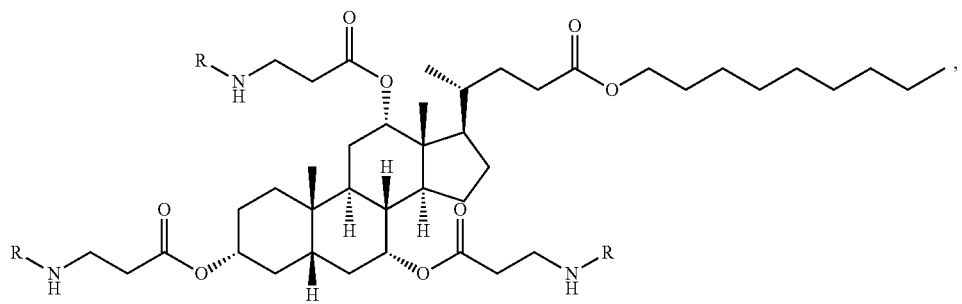
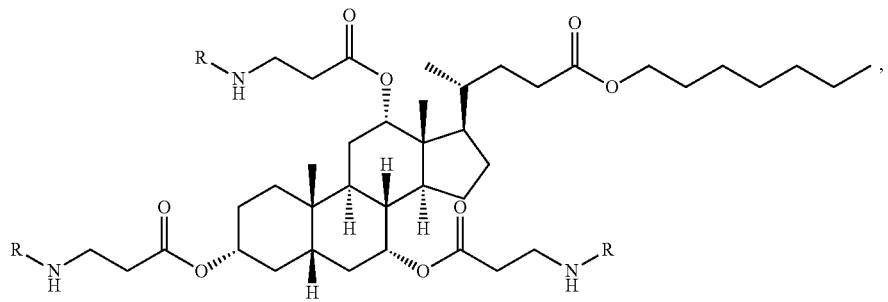

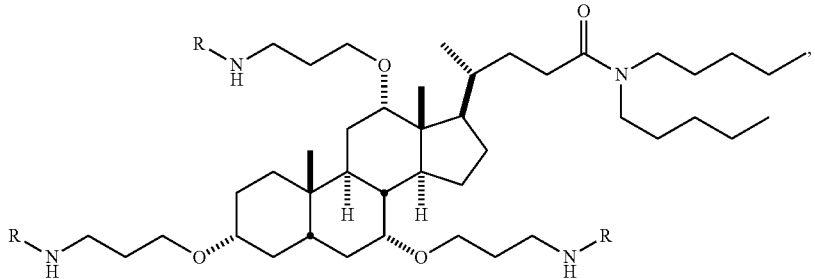

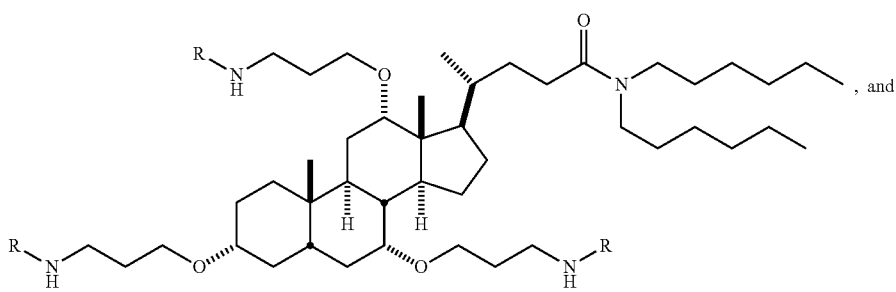
, and

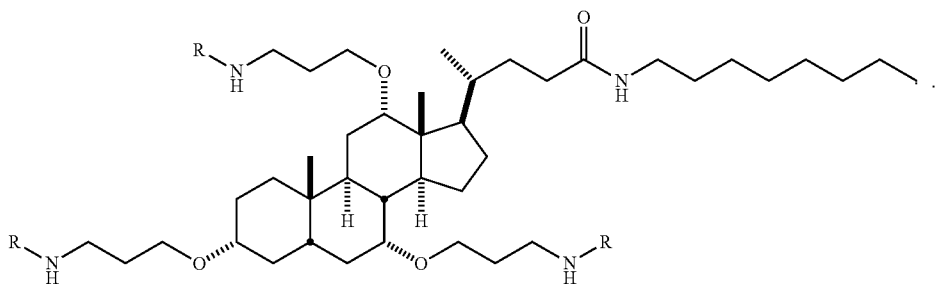
.

where R can be one or more cleavable groups, non-limiting examples of which are selected from the group consisting of $CH_2SO_3^-$ or salt thereof, such as $CH_2SO_3^-Na+$.

In some embodiments, a CSA prodrug is prepared by attaching an inactivating or cleavable group to the terminal cationic functional group of the CSA compound. For example, the cationic functional groups (e.g., amino or guanidino groups) of a CSA may be reacted to attach cleavable groups and produce compounds according to Formula I. The cleavable groups are such that upon addition of a CSA prodrug to a pharmaceutical formulation or upon administration of the CSA prodrug to a subject and/or upon exposure of the CSA prodrug to physiological conditions, the cleavable groups begin to be removed and the cationic functional groups are activated or more fully activated.

Non-limiting examples of cleavable groups that may be directly bound to amino groups are 9-fluorenymethyl carbamate, t-butyl carbamate, benzyl carbamate, acetamide, trifluoroacetamide, phthalimide, methane sulfonate ($—CH_2SO_3^-$), benzylamine, methoxymethylether, triphenylmethylamine, benzyideneamine and p-toluensufonamide and the like.

Any compound that can be converted in vivo to provide the bioactive agent (i.e., the CSA compound of formula II) is a prodrug within the scope and spirit of the invention.

In some embodiments, one or more of $R_3$, $R_7$ or $R_{12}$ include a cleavable group that is hydrolysable upon exposure to physiological conditions and/or upon exposure to a hydrolyzing agent during preparation of a pharmaceutical formulation. In a particular embodiment, the cleavable group is a sulfo group such as a sulfoalkyl group or other sulfonate containing group. For example, an inactivating group may be a sulfomethyl group.

In some embodiments, one or more of $R^1$ ($R_3$), $R^2$ ($R_7$) or $R^3$ ($R_{12}$) may include an amino terminal as the cationic functional group (e.g., -alkyl-$NH_2$), and the amino terminal may be masked or inactivated by a sulfoalkyl cleavable group (e.g., -alkyl-S($=O$)$_2$—O or -alkyl-S($=O$)$_2$—OH). For example, the CSA compound including an amino group at one or more of $R^1$ ($R_3$), $R^2$ ($R_7$) or $R^3$ ($R_{12}$) may be reacted with an alkanol sulfonate, such as methanol sulfonate (i.e. hydroxymethanesulfonic acid or alkali metal hydroxymethanesulfonate), in a dehydration reaction, upon which the one or more of $R^1$ ($R_3$), $R^2$ ($R_7$) or $R^3$ ($R_{12}$) becomes -alkyl-NH-methyl-S($=O$)$_2$—O$^-$, or salt thereof such as alkyl-NH-methyl-S($=O$)$_2$—O$^-$ Na$^+$, or -alkyl-NH-methyl-S($=O$)$_2$—OH. The cationic functional group is thereby inactivated by the sulfomethyl cleavable group, as shown in Scheme 1

Scheme 1

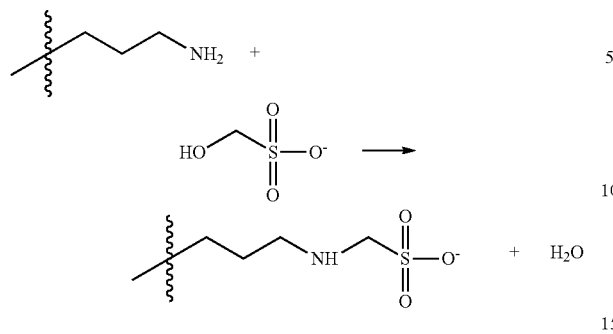

The sodium salt of methanol sulfonate can also be expressed as formaldehyde-sodium bisulfite adduct and can be used to form a prodrug according to Scheme 2.

Scheme 2

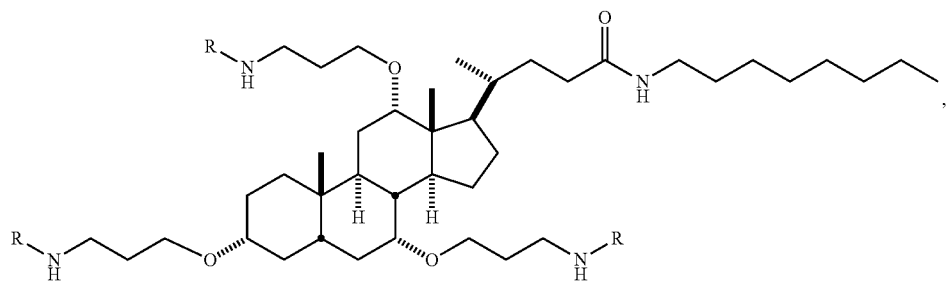

wherein R is selected from the group consisting of $CH_2SO_3^-Na^+$.

When desired, the one or more of $R^1$, $R^2$, or $R^3$ can be hydrolyzed (e.g., when exposed to physiological conditions upon administration or during preparation of a pharmaceutical formulation), thereby removing the sulfomethyl cleavable group and activating the amino cationic functional group, as shown in Scheme 3.

Scheme 3

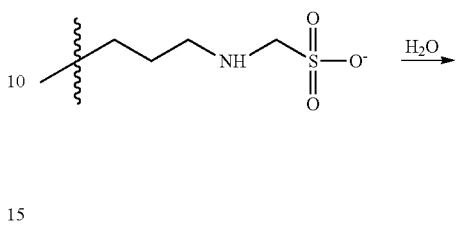

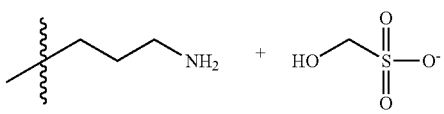

In some embodiments, the prodrug is the mono-, di-, tri- or tetra-methane sulfonate form of CSA-13:

wherein R is selected from the group consisting of $CH_2SO_3^-$ or salt thereof, such as $CH_2SO_3^-Na+$.

In some embodiments, the prodrug is the mono-, di-, tri- or tetra-methane sulfonate form of CSA-192:

wherein R is selected from the group consisting of $CH_2SO_3^-$ or salt thereof, such as $CH_2SO_3^-Na+$.

In some embodiments, activation of the prodrug to a more active form can occur through enzymatic action upon administration of the CSA prodrug to a subject and/or exposure to physiological conditions. In other embodiments, activation can occur through chemical (e.g., non-enzymatic) activation, such as through changes in pH, temperature, ionic conditions, and/or water content. The chemical activation can occur as a result of administration to a subject and/or exposure to physiological conditions, or during the preparation of a pharmaceutical formulation. In other embodiments, activation can occur through a combination of enzymatic activity and chemical activity.

In some embodiments, one or more inactivating groups may be attached to one or more functional cationic groups to form an enzyme sensitive group subject to alteration and/or removal upon exposure to an enzyme or class of enzymes. For example, an inactivating group may form an enzyme sensitive group sensitive to ligase, isomerase, lyase, transferase, hydrolase, and/or oxidoreductase classes of enzymes. In particular embodiments, an enzyme sensitive group may be sensitive to esterase, phosphatase, protease, amylase, lactase, lipase, azo-reductase, and/or nitroreductase enzymes. For example, an inactivating group may include an ester group sensitive to esterase enzymes, or an azo group sensitive to azo altering enzymes such as azo-reductase, or a nitro group sensitive to nitro altering enzymes such as nitro-reductase.

In some embodiments, the conversion of a CSA prodrug from inactive form to active form may have a rate dependent at least upon the structures of the CSA compounds and inactivating groups, the mode of administration, the specific physiological conditions within the subject and/or the chemical conditions within a prepared pharmaceutical formulation, and the mode of conversion from inactive to active form (e.g., enzymatic or chemical or both). For example, the conversion half-life of a CSA prodrug from inactive to active form may range from 1 minute or less to several days, several weeks, or even several months. For example, the conversion half-life may range from 1 to 60 minutes, from 1 to 24 hours, from 1 to 7 days, or from 1 to 4 weeks or longer. In other embodiments, the conversion half-life may be substantially immediate. For example, a pharmaceutical formulation may be prepared just prior to administration to a subject, and the conversion from inactive to active form may be complete or substantially complete upon administration to the subject.

Pharmaceutical Formulations

As discussed above, embodiments of CSA prodrug compositions may be formulated to exhibit an inactive or less active form until administration to a subject, upon which the prodrug compositions begin to convert to a more active form. In other embodiments, a CSA prodrug may exhibit an inactive form until it is incorporated into a pharmaceutical formulation, such as a carrier or excipient, useful for administration to a subject. For example, a CSA prodrug may begin to convert to a fully active form upon addition of the CSA prodrug to the pharmaceutical formulation during preparation of the pharmaceutical formulation.

Pharmaceutical formulations may include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions, and suspensions may also include suspending agents and thickening agents. Such carriers include tablets (coated or uncoated), capsules (hard or soft), microbeads, powder, granules and crystals. Supplementary active compounds (e.g., preservatives, antibacterial, antiviral and antifungal agents) can also be incorporated into the formulations.

In a particular example, a CSA prodrug may exhibit an inactive or less active form until it is added to a pharmaceutical formulation for use in an intravenous administration system. In this example, the CSA prodrug compound begins to convert to an active form upon preparation of the intravenous formulation. The pharmaceutical formulation may, for example, be located in an intravenous administration bag or other container, and the CSA prodrug may be added to the other ingredients of the intravenous formulation (e.g., saline solution) already in the intravenous bag/container, whereupon the CSA prodrug begins to convert from an inactive or less active form to a fully active form.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The prodrugs of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Useful pharmaceutical dosage-forms for administration of the prodrugs of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Exemplary compositions for administration of the prodrugs of formula I are liposomal delivery compositions. Liposomes are an artificially-prepared spherical vesicle composed of a lamellar phase lipid bilayer. The liposome can be used as a vehicle for administration of nutrients and pharmaceutical drugs. Liposomes can be prepared by disrupting biological membranes (such as by sonication). Liposomes are often composed of phosphatidylcholine-enriched phospholipids and may also contain mixed lipid chains with surfactant properties such as egg phosphatidylethanolamine. A liposome design may employ surface ligands such as, for example, albumin for attaching to unhealthy tissue. The major types of liposomes are the multilamellar vesicle (MLV), the small unilamellar liposome vesicle (SUV), the large unilamellar vesicle (LUV), and the cochleate vesicle.

Exemplary compositions for nasal or pulmonary aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Injectables

A parenteral composition suitable for administration by injection can be prepared by stirring 1.5% by weight of active ingredient in 10% by volume propylene glycol and water. The solution is sterilized by commonly used techniques.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The antimicrobial prodrugs of this invention can be administered as treatment for the control or prevention of bacterial or fungal infections by any means that produces contact of the active agent with the agent's site of action in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram (mg/kg) of body weight, with the preferred dose being about 0.01 to about 100 mg/kg; with the more preferred dose being about 0.01 to about 30 mg/kg. Advantageously, compounds of the present invention may be administered in a single daily dose, or the total daily dosage may be administered in divided doses of two, three, or four times daily.

Dosage forms of compositions suitable for administration contain from about 0.5 mg to about 100 mg of active ingredient per unit. In these pharmaceutical compositions the active ingredient will ordinarily be present in an amount of about 0.5% to about 95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Combinations

In another embodiment, the present invention provides methods of treating a patient comprising administering to a patient in need of treatment a therapeutically effective amount of a prodrug or a pharmaceutically acceptable salt, or a stereoisomer, or a solvate or a polymorph thereof according to formula I and an anti-microbial agent. In embodiments, the prodrug and the anti-microbial agent may be administered simultaneously or sequentially. In embodiments, the prodrug and the anti-microbial agent may be administered in a single composition.

In a further embodiment, the present invention provides a pharmaceutical combination comprising a prodrug or a pharmaceutically acceptable salt, or a stereoisomer, or a solvate or a polymorph thereof of formula I and an anti-microbial agent. In embodiments, the anti-microbial agent may be selected from the group consisting of: amikacin, bacitracin, colistin, gentamicin, kanamycin, metronidazole, mupirocin, neomycin, netilmicin, polymyxin B, streptomycin, tobramycin, phenols and cresols such as 2,4-dichloro-sym-metaxylenol, parachlorometaxylenol, and parachlorometacresol, bisphenols such as hexachlorophene, dichlorophene, bithionol, triclosan, and fentichlor, salicylanilides such as 4',5-dibromsalicylanilide, 3',4',5-trichlorosalicylanilide, 3',4',5-tribromosalicylanilide, and 3,5,dibromo-3'-trifluoromethyl-salicylanilide, carbanilides such as trichlorocarbanilde and 3-trifluoromethyl-4-4'-dichlorocarbanilide, quaternary ammonium compounds such as alkyl-dimethyl benzyl ammonium chloride, alkyl-trimethyl ammonium chloride, alkyl trimethyl ammonium bromide, cetyl-trimethyl ammonium bromide, B-phenoxyethyl-dimethyl-dodecyl ammonium bromide, p-tert-octylphenoxyethoxyethyl-dimethyl-benzyl ammonium chloride, tetradecyl-pyridinium bromide, cetyl pyridinium bromide, cetyl pyridinium chloride, di-(n-octyl)-dimethyl ammonium bromide, alkyl-isoquinolinium bromide, 1-(3-chloroallyl)-3-5-7-triaza-1-azoniaadamantane chloride, and chlorhexidine (1,6,di(N-p-chlorophenylguanidino)hexane), 2-bromo-2-nitropropan-1,3-diol, imidazonidyl urea, ethanol, isopropyl alcohol, natural oils, aqueous and organic extracts of natural or synthetic substances, tea tree oil, and mixtures thereof.

The present invention includes within its scope pharmaceutical compositions comprising, as an active ingredient, a therapeutically effective amount of at least one of the prodrugs of formula I, alone or in combination with a pharmaceutical carrier or diluent. Optionally, the prodrugs of the present invention can be used in combination with other suitable therapeutic agents useful in the treatment of the aforementioned disorders including: agents used to treat respiratory conditions, anti-inflammatory agents; antibiotics; antifungals and analgesics.

The prodrugs described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, Arcoxia®, and Bextra®), CTLA4-Ig agonists/antagonists, CD40 ligand antagonists, IMPDH inhibitors, such as mycophenolate (CellCept®), integrin antagonists, α-4 β-7 integrin antagonists, cell adhesion inhibitors, interferon gamma antagonists, ICAM-1 inhibitor, tumor necrosis factor (TNF) antagonists (e.g., infliximab, OR1384, including TNF-α inhibitors, such as tenidap, anti-TNF antibodies or soluble TNF receptor such as etanercept (Enbrel®), Remicade®, rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Such other therapeutic agent(s) may be administered prior to, simultaneously with, or following the administration of the prodrugs in accordance with the invention.

The above other therapeutic agents, when employed in combination with the compounds of the present invention, may be used, for example, in those amounts indicated in the Physicians' Desk Reference (PDR) or as otherwise determined by one of ordinary skill in the art.

Administration

As discussed above, embodiments of CSA prodrug compositions may be formulated to exhibit an inactive or less active form until administration to a subject, upon which the prodrug compositions begin to convert to a more active form.

A "subject" refers to a human or an animal, such as but not limited to non-human primates (e.g., apes, gibbons, gorillas, chimpanzees, orangutans, macaques), domestic animals (e.g., dogs and cats), farm animals (e.g., pigs, chickens, turkeys, ducks, geese, horses, cows, goats, sheep, bison, buffalos), experimental animals (e.g., mice, rats, rabbits, guinea pigs), wild animals (e.g., pigeons, hawks, eagles, lions, tigers, bears, elephants), birds, reptiles, amphibians, and humans. Subjects include animal models, for example, a mouse model of an infection. Subjects include naturally occurring or non-naturally occurring mutated or non-human genetically engineered (e.g., transgenic or knockout) animals. Subjects further include animals having or at risk of having an infection. Subjects can be any age. For example, a subject (e.g., human) can be a newborn, infant, toddler, child, teenager, or adult, e.g., 50 years or older. The term "subject" may also refer to a sample, such as a tissue sample, biopsy, or other form of biological material used in testing, diagnosis, and/or research.

"Administration" refers to any method of delivery of the CSA prodrug and/or pharmaceutical formulation thereof to a subject. The prodrugs of the present invention can be administered in an effective amount within the dosage range of about 0.2 to 1000 mg, preferably from about 1 to 100 mg in a regimen of single, two or four divided daily doses.

Exemplary routes of administration include, for example: orally, such as in the form of tablets, capsules, granules or powders; sublingually; bucally; parenterally, such as by subcutaneous, intravenous, intramuscular, or intracisternal injection or infusion techniques (e.g., as sterile injectable aqueous or non-aqueous solutions or suspensions); nasally, including administration to the nasal membranes, such as by inhalation spray; topically, such as in the form of a cream or ointment; inhalation, such as by nasal or pulmonary inhalation, such as in the form of a spray or aerosol; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Administration may be to any biological fluid or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis).

Utilities & Uses

The present invention provides methods of treating a patient suffering from a disease or disorder selected from the group consisting of: fungal infections, bacterial infections, multiple myelomas and cystic fibrosis, comprising administering to the patient a therapeutically effective amount of a prodrug or a pharmaceutically acceptable salt, or a stereoisomer, or a solvate or a polymorph thereof according to formula I.

The prodrugs of the present invention are antimicrobial agents useful for the treatment or prevention of a bacterial or fungal infection or both bacterial and fungal infections in a subject or an organism. In this context, the fungal infection can be caused by yeast or a non-yeast fungus. The fungal infection may, for example, be caused by fungi of the species *Candida albicans, Candida tropicalis, Candida (Clasvispora) lusitaniae, Candida (Pichia) guillermondii, Lodderomyces elongisporus, Debaryomyces hansenii, Pichia stipitis* (see also Rossignol T. et al, Nucleic Acids Research, 2008, 36:D557-D561), *Asperigillus fumigatus, Blastomyces dermatitidis, Cladophialophora bantiana, Coccidioides immitis, Cryptococcus neoformans, Fusarium* spp., *Microsporum* spp., *Penicillium marneffei* or *Trichophyton* spp.

The bacterial infection may be caused by a Gram negative or a Gram positive bacterium. The bacterial infection may, for example, be caused by bacteria of the genus *Acinetobacter, Actinomyces, Aeromonas, Bordetella, Borrelia, Brucella, Burkholderia, Campylobacter, Chlamydia, Clostridium, Corynebacterium, Enterococcus, Erwinia, Escherichia, Francisella, Haemophilus, Helicobacter, Klebsiella, Legionella, Leptospira, Listeria, Mycobacterium, Mycoplasma, Neisseria, Pseudomonas, Rickettsia, Salmonella, Shigella, Staphylococcus, Streptococccus, Treponema, Veillonella, Vibrio* or *Yersinia*. In one particular embodiment, the infection is caused by *Staphylococcus aureus, Mycobacterium smegmatis, Pseudomonas aeruginosa, Burkholderia cepacia, Klebsiella pneumonia, Aeromonas hydrophila, Erwinia carotovora, Erwinia chrysanthemi*, or *Escherichia coli*.

Further, the prodrugs of the invention are useful for the treatment of mammalian in particular human diseases caused by bacteria through interference of bacterial physiology. Such diseases include endocarditis, respiratory and pulmonary infections (preferably in immunocompromized and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis which all can be triggered by *Pseudomonas aeruginosa*, for example. Furthermore, the compounds can, for example, also be used for the treatment of pulmonary infections caused by *Burkholderia cepacia* (preferably in immunocompromized and cystic fibrosis patients), gastroenteritis and wound infections caused by *Aeromonas lcydrophila*, sepsis in tropical and subtropical areas caused by *Chrofnobacterium violaceum*, diarrhoea with blood and haemolytic uremic syndrome (HUS) caused by *Escherichia coli*, yersiniosis triggered by *Yersinia enterocolitica* and *Y. pseudotuberculosis*, and transfusion-related sepsis and fistulous pyoderma caused by *Serratia liquefaciens*, to name only a few.

Synthesis

The prodrugs of the present invention can be prepared in a number of ways well known to one skilled in the art of organic synthesis. The prodrugs of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel prodrugs of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all prodrugs of Formula I falling into a given class may be compatible with some of the reaction conditions required in some of the methods described. Such restrictions to the substituents, which are compatible with the reaction conditions, will be readily apparent to one skilled in the art and alternate methods must be used.

The prodrugs of formula I may be prepared by the procedure depicted in Scheme 2, that depicts reacting the CSA compounds of formula IV having one or more amine functional groups with a methane sulfonate amine protecting group. To prepare such a methane sulfonate protected prodrug of formula I a CSA compound of formula IV having one or more amine functional groups is combined with a formaldehyde-sodium bisulfite adduct in an aqueous solution. The resulting mixture is heated to reflux and maintained at that temperature for a sufficient time to complete the reaction such as, for example, 48 h. The solution may then be frozen at a sufficient temperature such as, for example, −70° C. and the water may be removed via any conventional method known to one of skill in the art such as, for example, lyophilization to yield the desired methane sulfonate protected prodrug.

Scheme 2

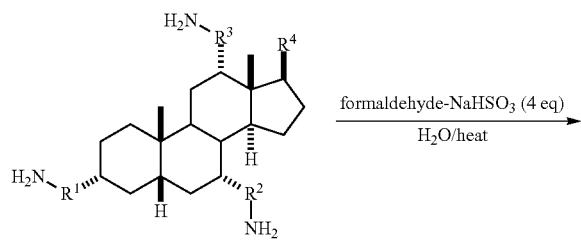

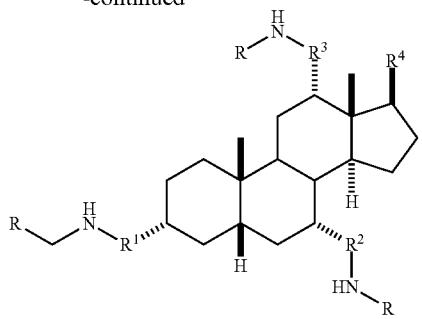

wherein R is selected from the group consisting of $CH_2SO_3^-$ or salt thereof, such as $CH_2SO_3^-Na^+$.

Although only a few example embodiments have been described in detail above, those skilled in the art will readily appreciate that many modifications are possible in the example embodiments without materially departing from this disclosure. Accordingly, all such modifications are intended to be included within the scope of this disclosure.

EXAMPLES

Compounds described herein can be prepared by known methods, such as those disclosed in U.S. Pat. No. 6,350,738 and other references discussed in this application, which are incorporated herein by reference. A skilled artisan will readily understand that minor variations of starting materials and reagents may be utilized to prepare known and novel cationic steroidal antimicrobials. For example, the preparation of CSA-13 disclosed in U.S. Pat. No. 6,350,738 (compound 133) can be used to prepare CSA-92 by using hexadecylamine rather than octyl amine as disclosed.

Example 1

Preparation of mono-, di-, tri and tetra-methane sulfonate prodrugs of CSA compound CSA-13 can be made according to Scheme 4:

Scheme 4

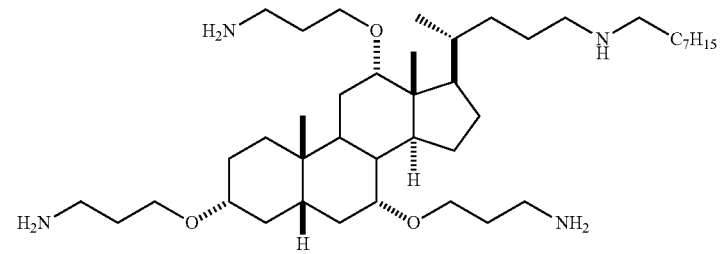

formaldehyde-NaHSO₃ (4 eq)
H₂O/heat

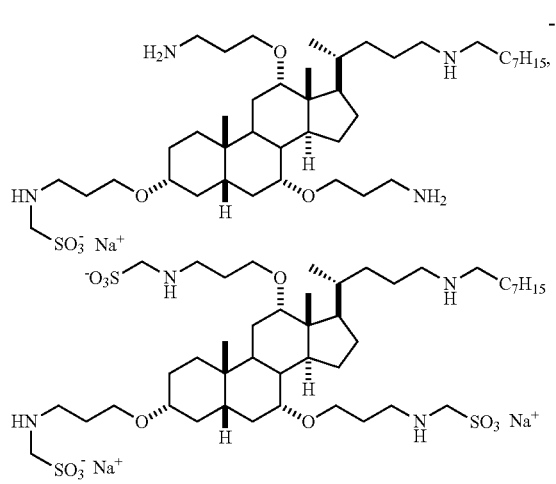

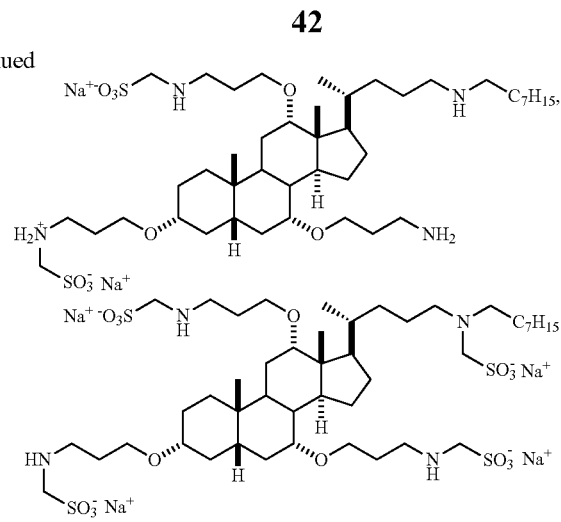

and

CSA compound CSA-13 was prepared by the processes and methods described in U.S. Pat. No. 6,350,738. CSA-13 (220 mg, 0.325 mmol) and formaldehyde-sodium bisulfite adduct (174.5 mg, 1.30 mmol) were added to water (6 mL). The reaction mixture was heated and maintained at reflux for 48 h. After cooling the reaction mixture was frozen at −70° C. and the water was removed via lyophilization to yield a light yellow solid. Structure was confirmed by mass spectrometry.

Examples 2-17

It is anticipated that methane sulfonate prodrugs of CSA compounds CSA-8, 44, 90, 92, 131, 134, 136, 137, 138, 142, 144, 145, 146, 190, 191, and 192 as depicted in Table 1, may similarly be prepared according to the procedure described in Example 1 but by substituting these CSA compounds for CSA-13.

TABLE 1

| Ex. | CSA No. | Structure |
|---|---|---|
| 2 | 8 | ![structure] |
| 3 | 44 | ![structure] |
| 4 | 90 | ![structure] |

TABLE 1-continued

| Ex. | CSA No. | Structure |
|---|---|---|
| 5 | 92 | 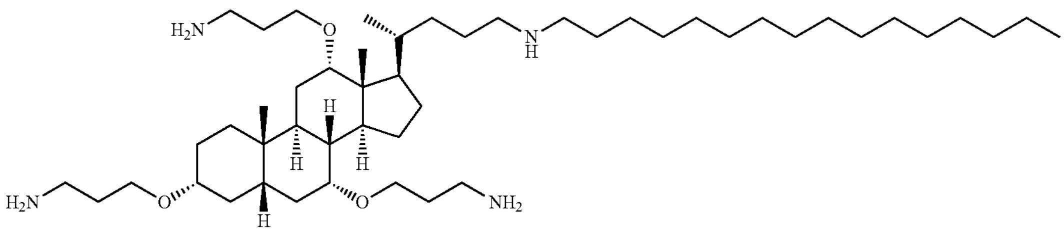 |
| 6 | 131 | 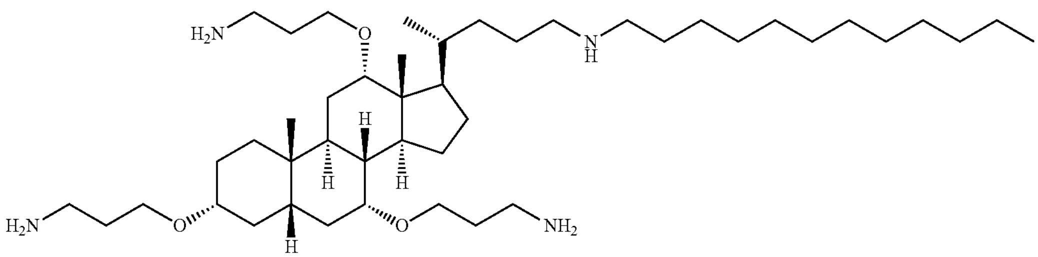 |
| 7 | 134 | 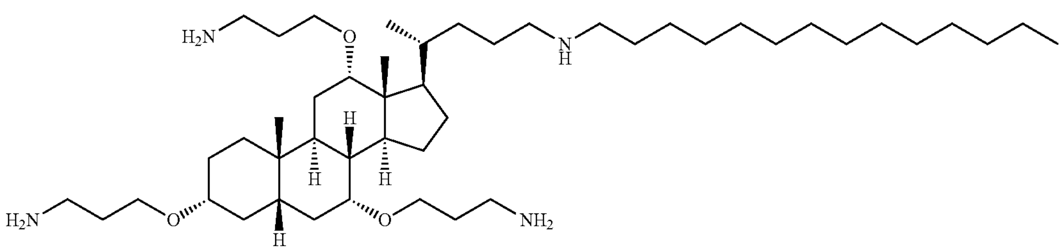 |
| 8 | 136 | 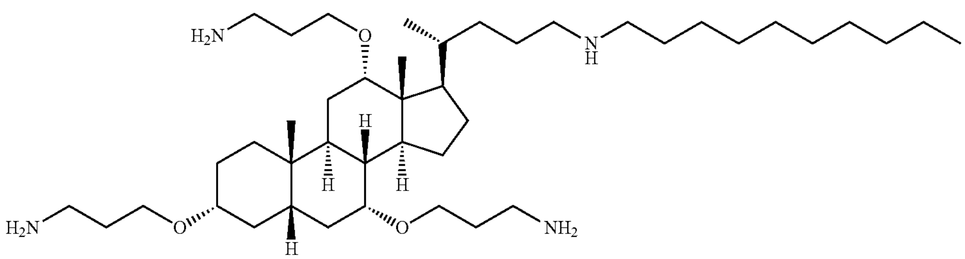 |
| 9 | 137 | 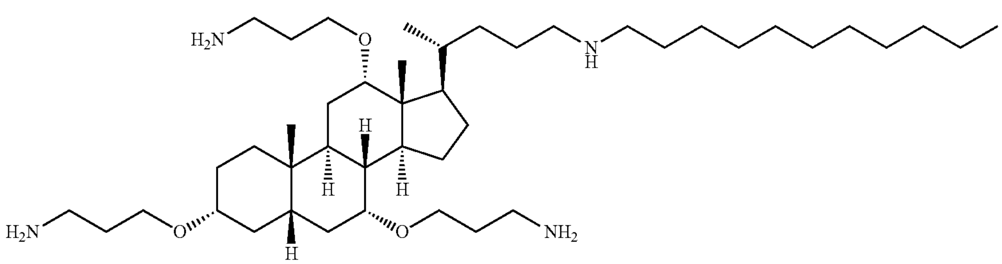 |
| 10 | 138 | 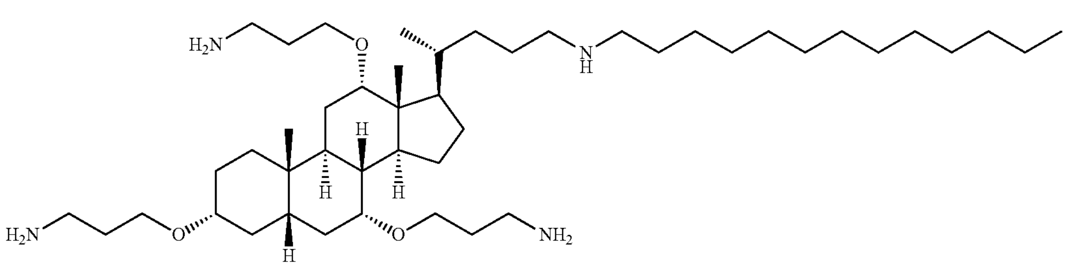 |

TABLE 1-continued

| Ex. | CSA No. | Structure |
|---|---|---|
| 11 | 142 | 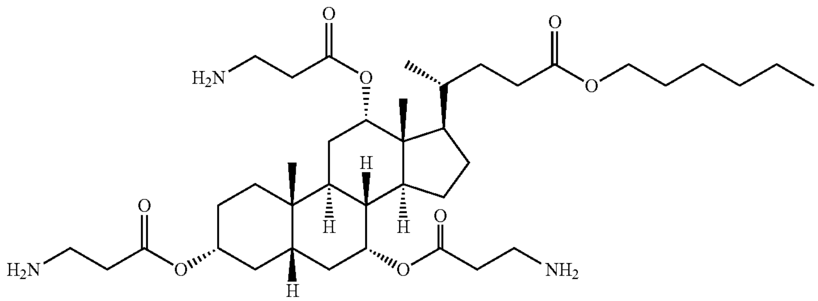 |
| 12 | 144 | 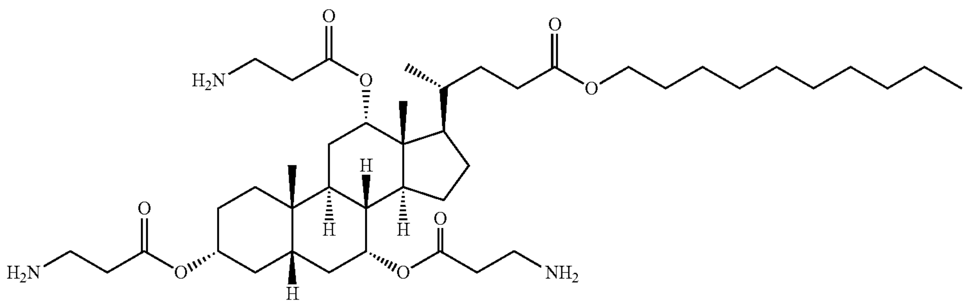 |
| 13 | 145 | 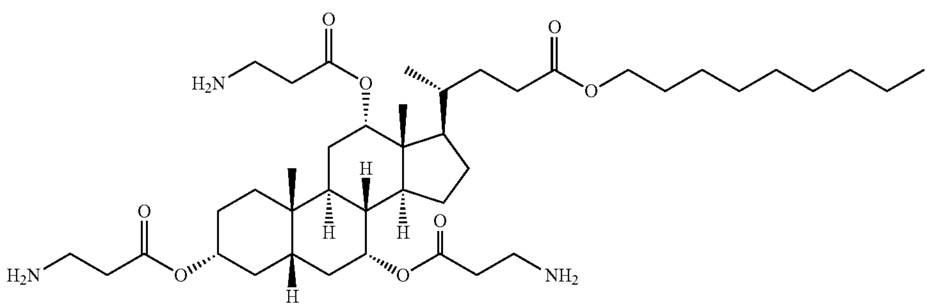 |
| 14 | 146 | 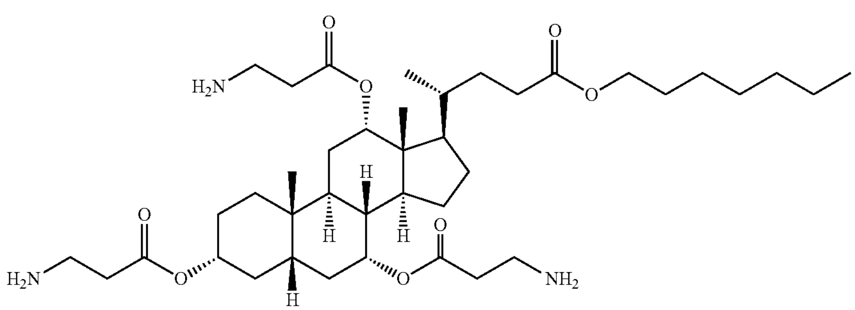 |
| 15 | 190 | (HCl)₄ |

TABLE 1-continued

| Ex. | CSA No. | Structure |
|---|---|---|
| 16 | 191 | 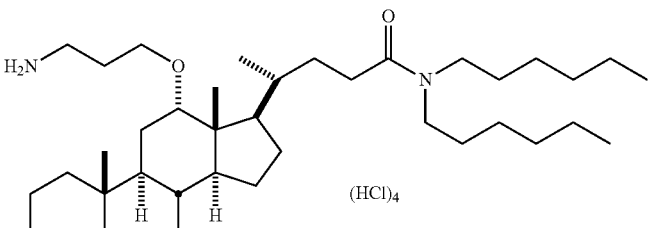 (HCl)₄ |
| 17 | 192 | 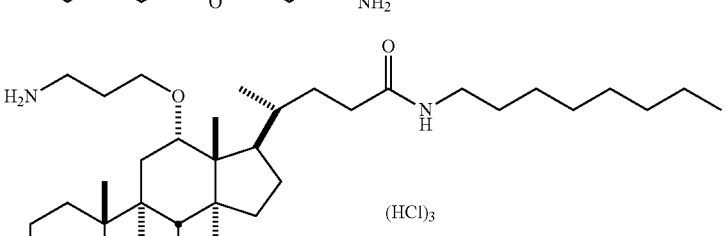 (HCl)₃ |

Example 18

Kinetic Data (CSA-13 MS)

Kinetic minimum inhibitory concentrations (MIC) of the cationic steroidal antimicrobial prodrug of CSA-13 (CSA-13 MS) at various concentrations and controls are listed as the number of colony forming units per milliliter versus time below in Table 2. FIG. 1 is a graph showing Kinetic MIC's for CSA-13 MS.

TABLE 2

| µg/mL | 0.5 h | 1.0 h | 1.5 h | 2.0 h | 3.0 h | 4.0 h | 6.0 h | 8.0 h | 12.0 h | 24.0 h |
|---|---|---|---|---|---|---|---|---|---|---|
| 4 | 5.00 | 1.00 | 1.50 | 2.00 | 3.00 | 4.00 | 6.00 | 8.00 | 1.60 | 2.40 |
| 8 | 1.95 | 3.81 | 1.19 | 1.23 | 9.21 | 9.04 | 3.36 | 8.19 | 4.64 | 1.00 |
| 16 | 1.26 | 1.00 | 1.00 | 1.00 | 1.00 | 1.00 | 1.00 | 1.00 | 1.00 | 1.00 |
| 32 | 4.64 | 1.00 | 1.00 | 1.00 | 1.00 | 1.00 | 1.00 | 1.00 | 2.71 | 1.00 |
| C1 | 4.50 | 4.28 | 6.83 | 6.82 | 2.49 | 1.40 | 8.18 | 2.64 | 7.31 | 2.19 |
| C2 | 3.33 | 3.11 | 5.44 | 4.33 | 1.33 | 4.08 | 2.17 | 4.20 | 5.97 | 2.74 |

Example 19

Pharmacological Analysis

The pharmacological analysis of the methane sulfonate prodrug of CSA-13 (CSA-13 MS) versus the free base CSA-13 compound was assessed for their antimicrobial properties against the ATCC 25923 strain of *staphylococcus aureus* (hereinafter "staph A"). The methane sulfonate prodrug exhibited a minimum inhibitory concentration (hereinafter "MIC") of 0.4 µg/ml; whereas the free amino compound exhibited a MIC of 1.6 µg/ml.

Example 20

Toxicity Analysis

Methane-sulfonate prodruge of CSA-13 (CSA-13 MS) toxicity study in rats. No treatment related changes were observed and there are no clinical signs, body weight and gross pathology for the animals which are treated with CSA-13-MS at 30 mg/kg (SC and IV).

Example 21

Toxicity Study (CSA-192 MS)

Figure 2:
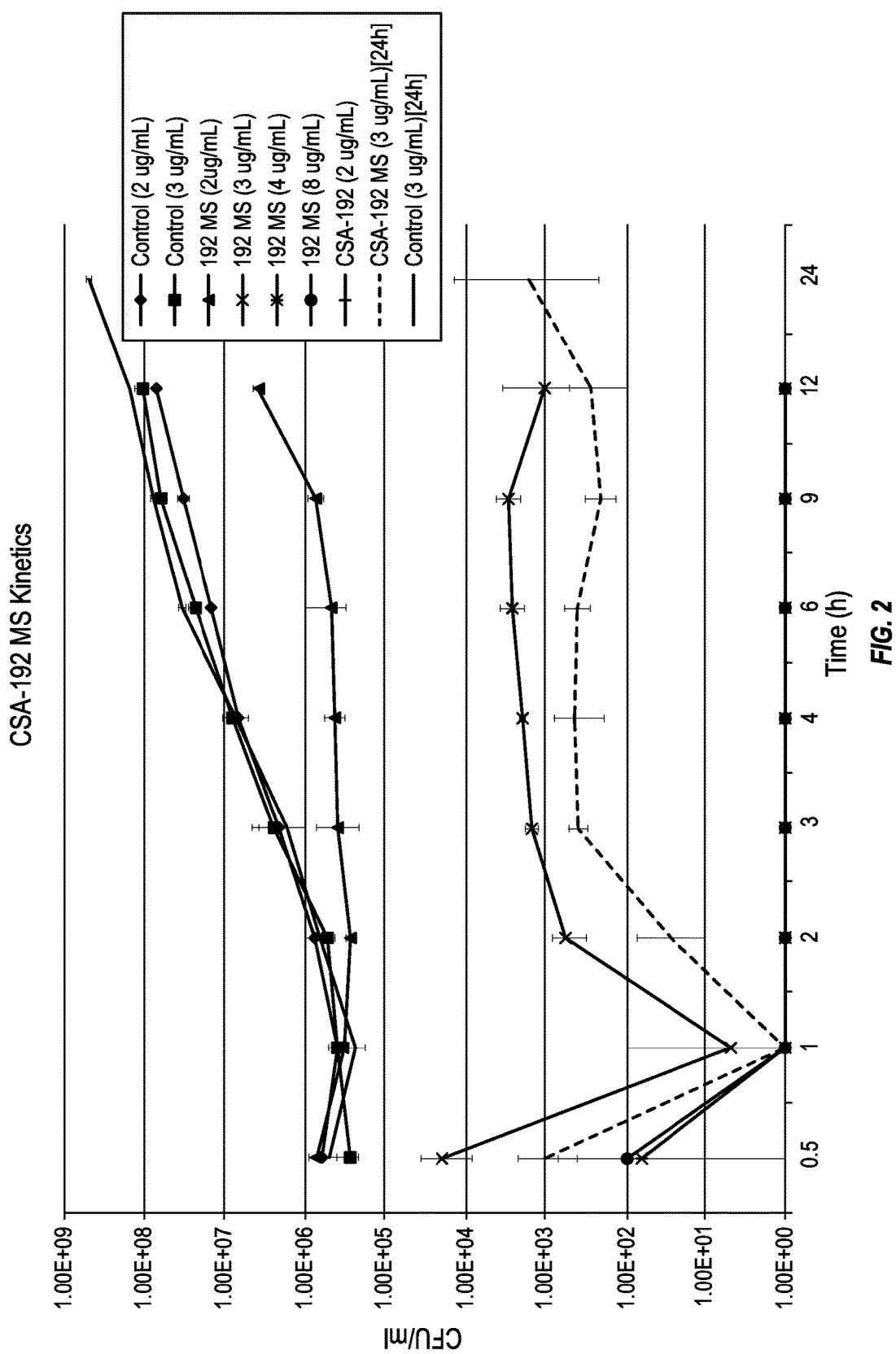
FIG. 2 is a chart that graphically illustrates Kinetic Minimum Inhibitory Concentrations of Cationic Steroidal Antimicrobial prodrug CSA-192 MS (illustrated as colony forming units per milliliter versus time).

The objective of this study was to determine the Maximum Tolerated Dose (MTD) of CSA-192 MS following intravenous (i.v.) administration at various dose levels in C57BL/6 female mice. FIG. 2 is a graph showing CSA-192 MS Kinetics.

Immunocompetent C57BL/6 female mice weighing 16 to 20 g were obtained from the University of Sevilla's facility. The number of animals that were selected for use in this study was considered to be the minimum requirement to meet rational scientific endpoints.

Throughout the study period, the experimental animals were housed in the animal facility of the Biomedicine Institute of Seville (IBiS). The animals were housed 6 mice per cage in sterilized suspended polycarbonate cages (cage size: approximately L 400 mm×B 220 mm×H 175 mm), with stainless steel top grills having facilities for holding pellet food and drinking water in bottle with stainless steel sipper tube. All mice had free access to water and standard pelleted laboratory animal diet ad libitum.

Throughout the acclimatization and treatment period the temperature and humidity were in the range of 20.0° C. to 24.0° C. and ≤55% RH, respectively. Duration of illumination in the testing unit was controlled to give 12 hours light (08.00 to 20.00) and 12 hours dark cycle during the 24-hour period. Animal rooms were ventilated at the rate of 15-25 air changes per hour.

One the first day of the study, mice were subjected to randomization and allocated to different groups, so that each group (G) contains 6 females. Each cage housed 6 mice. Each cage was identified by a cage card, with details like study item, species, strain, sex, number of animals, date, dose, and investigator name.

The study was conducted at four different dose levels. On day 1 of treatment all the animals in G1, G2, G3, and G4 groups were administered with CSA-192 MS at 4, 8, 16, and 32 mg/kg based on their body weight. Dose volumes were maintained at 0.2 mL for G1, G2, and G3. The dose volume for G4 was 0.32 mL.

More particularly, the test item was administered by intravenous route, at dose concentration of 4 mg/kg body weight for G1, 8 mg/kg body weight for G2, 16 mg/kg body weight for G3, and 32 mg/kg body weight G4 groups, respectively. Dose volumes were maintained at 0.2 mL for G1, G2, and G3. For group G4 the dose volume was 0.32 mL. The details of experimental groups and doses are presented in Table 3.

TABLE 3

| Group | Dose (mg/Kg b.w) | Dose Volume (mL) | No of Mice | Sex |
|---|---|---|---|---|
| G1 | 4 | 0.2 | 6 | Female |
| G2 | 8 | 0.2 | 6 | Female |
| G3 | 16 | 0.2 | 6 | Female |
| G4 | 32 | 0.32 | 6 | Female |

All the animals were observed for 7 days post dosing to study their general condition/reaction to the dose administration and mortality. The first day they were checked immediately after dose administration, at 30 min, 1 hour, and every 4 hours, the following days twice a day. Mice were sacrificed on day 7 of the study period.

There were no incidences of mortality and abnormal clinical signs in mice treated intravenously with CSA-192 MS at doses of 4.0 mg/kg body weight (G1), 8.0 mg/kg body weight (G2), and 32.0 mg/kg body weight (G4). At a dose of 16.0 mg/kg body weight (G3) one animal showed signs of somnolence (sleepiness) immediately after administration, but this reaction disappeared after an hour post dose administration; however, the rest of mice in G3 did not present signs. The number of clinical observations per number of animals per group is set forth in Table 4.

TABLE 4

| | Clinical observations/No of animals per group | | | |
|---|---|---|---|---|
| Day | G1 4 mg/Kg | G2 8 mg/kg | G3 16 mg/kg | G4 32 mg/kg |
| 1 | 0/6 | 0/6 | 1/6 | 0/6 |
| 2 | 0/6 | 0/6 | 0/6 | 0/6 |
| 3 | 0/6 | 0/6 | 0/6 | 0/6 |
| 4 | 0/6 | 0/6 | 0/6 | 0/6 |
| 5 | 0/6 | 0/6 | 0/6 | 0/6 |
| 6 | 0/6 | 0/6 | 0/6 | 0/6 |
| 7 | 0/6 | 0/6 | 0/6 | 0/6 |

No treatment related change in body weight was observed in all groups treated with CSA-192 MS in survivor mice. In addition, no mortality was observed in animals administered with test item in any of the groups, as indicated in Table 5.

TABLE 5

| | No of animals found dead/No. of animals per group | | | |
|---|---|---|---|---|
| Day | G1 4 mg/Kg | G2 8 mg/kg | G3 16 mg/kg | G4 32 mg/kg |
| 1 | 0/6 | 0/6 | 0/6 | 0/6 |
| 2 | 0/6 | 0/6 | 0/6 | 0/6 |
| 3 | 0/6 | 0/6 | 0/6 | 0/6 |
| 4 | 0/6 | 0/6 | 0/6 | 0/6 |
| 5 | 0/6 | 0/6 | 0/6 | 0/6 |
| 6 | 0/6 | 0/6 | 0/6 | 0/6 |
| 7 | 0/6 | 0/6 | 0/6 | 0/6 |

Based on findings of the study, the MTD of CSA-192 MS may be considered to be at least 32.0 mg/kg of body weight in female C57BL/6 mice.

The subject of the present disclosure may be embodied in other specific forms without departing from its spirit or essential characteristics. The described embodiments are to be considered in all respects only as illustrative and not restrictive. In fact, any combination of the features disclosed in any of the foregoing embodiments can be combined. Embodiments can incorporate any combination of the different features described herein, such that components and elements from one embodiment can be incorporated into or replace elements from any of the other embodiments described herein.

What is claimed is:

1. A prodrug according to formula I:

wherein

A is a cationic steroidal antimicrobial (CSA) compound, or a pharmaceutically acceptable salt thereof, a stereoisomer thereof, or a solvate thereof, or a polymorph thereof, the CSA compound having 1 to 4 cationic functional groups, each with an amino terminal;

B is a cleavable group (C.G.) bonded to the amino terminal of a corresponding cationic functional group; and n is an integer selected from the group consisting of 1, 2, 3, and 4.

2. The prodrug of claim 1, wherein the CSA compound has a structure according to at least one of Formulae III or IV:

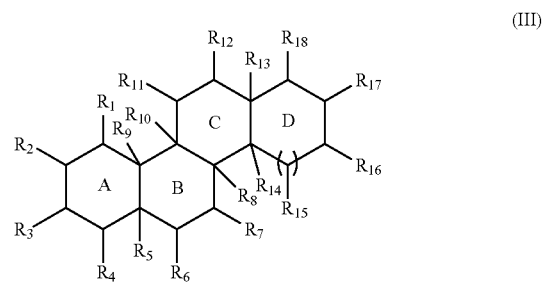

-continued

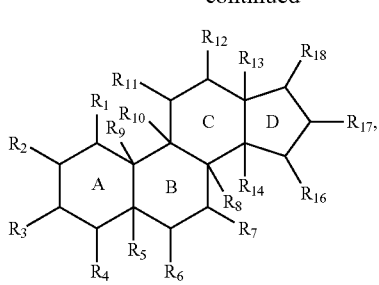

(IV)

where,
rings A, B, C, and D are independently saturated, or are fully or partially unsaturated, provided that at least two of rings A, B, C, and D are saturated;

$R_1$ through $R_4$, $R_6$, $R_7$, $R_{11}$, $R_{12}$, $R_{15}$, $R_{16}$, $R_{17}$, $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl or C.G.-aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy or C.G.-aminoalkyloxy, a substituted or unsubstituted aminoalkyloxyalkyl or C.G.-aminoalkyloxyalkyl, a substituted or unsubstituted aminoalkylcarboxy or C.G.-aminoalkylcarboxy, a substituted or unsubstituted aminoalkylaminocarbonyl or C.G.-aminoalkylaminocarbonyl, a substituted or unsubstituted aminoalkylcarboxamido or C.G.-aminoalkylcarboxamido, a substituted or unsubstituted di(alkyl)aminoalkyl, $H_2N$—$HC(Q_5)$-$C(O)$—O— or C.G.-HN—HC($Q_5$)-$C(O)$—O—, $H_2N$—HC($Q_5$)-$C(O)$—N(H)— or C.G.-HN—HC($Q_5$)-$C(O)$—N(H)—, a substituted or unsubstituted azidoalkyloxy or C.G.-azidoalkyloxy, a substituted or unsubstituted cyanoalkyloxy or C.G.-cyanoalkyloxy, a substituted or unsubstituted guanidinoalkyloxy or C.G.-guanidinoalkyloxy, a substituted or unsubstituted quaternary ammonium alkylcarboxy or C.G.-quaternary ammonium alkylcarboxy, and a substituted or unsubstituted guanidinoalkyl carboxy or C.G.-guanidinoalkyl carboxy, where $Q_5$ is a side chain of any amino acid (including a side chain of glycine, i.e., H) and C.G. is a cleavable group;

$R_5$, $R_8$, $R_9$, $R_{10}$, $R_{13}$, $R_{14}$, and $R_{17}$ are independently deleted when one of rings A, B, C, or D is unsaturated so as to complete the valency of the carbon atom at that site, or $R_5$, $R_8$, $R_9$, $R_{10}$, $R_{13}$, $R_{14}$, and $R_{17}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl or C.G.-aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy or C.G.-aminoalkyloxy, a substituted or unsubstituted aminoalkylcarboxy or C.G.-aminoalkylcarboxy, a substituted or unsubstituted aminoalkylaminocarbonyl or C.G.-aminoalkylaminocarbonyl, a substituted or unsubstituted di(alkyl)aminoalkyl, $H_2N$—HC($Q_5$)-$C(O)$—O— or C.G.-HN—HC($Q_5$)-$C(O)$—O—, $H_2N$—HC($Q_5$)-$C(O)$—N(H)— or C.G.-HN—HC($Q_5$)-$C(O)$—N(H)—, azidoalkyloxy or C.G.-azidoalkyloxy, cyanoalkyloxy or C.G.-cyanoalkyloxy, guanidinoalkyloxy or C.G.-guanidinoalkyloxy, and guanidinoalkylcarboxy or C.G.-guanidinoalkylcarboxy, where $Q_5$ is a side chain of any amino acid, and C.G. is a cleavable group;

provided that at least one of $R_{1\text{-}4}$, $R_6$, $R_7$, $R_{11}$, $R_{12}$, $R_{15}$, $R_{16}$, $R_{17}$, or $R_{18}$ is independently selected from the group consisting of a substituted or unsubstituted C.G.-aminoalkyl, a substituted or unsubstituted C.G.-aminoalkyloxy, a substituted or unsubstituted C.G.-aminoalkylcarboxy, a substituted or unsubstituted C.G.-aminoalkyloxyaminoalkylaminocarbonyl, a substituted or unsubstituted C.G.-aminoalkylaminocarbonyl, a substituted or unsubstituted C.G.-aminoalkylcarboxyamido, an C.G.-quaternary ammonium alkylcarboxy, C.G.-HN—HC($Q_5$)-$C(O)$—O—, C.G.-HN—HC($Q_5$)-$C(O)$—N(H)—, C.G.-azidoalkyloxy, C.G.-cyanoalkyloxy, a substituted or unsubstituted C.G.-guanidinoalkyloxy, and a substituted or unsubstituted C.G.-guanidinoalkylcarboxy.

3. The prodrug of claim 2, wherein at least one of $R_3$, $R_7$, or $R_{12}$ is independently selected from the group consisting of a substituted or unsubstituted C.G.-aminoalkyl, a substituted or unsubstituted C.G.-aminoalkyloxy, a substituted or unsubstituted C.G.-aminoalkylcarboxy, a substituted or unsubstituted C.G.-aminoalkyloxyaminoalkylaminocarbonyl, a substituted or unsubstituted C.G.-aminoalkylaminocarbonyl, a substituted or unsubstituted C.G.-aminoalkylcarboxyamido, an C.G.-quaternary ammonium alkylcarboxy, C.G.-HN—HC($Q_5$)-$C(O)$—O—, C.G.-HN—HC($Q_5$)-$C(O)$—N(H)$_{13}$, C.G.-azidoalkyloxy, C.G.-cyanoalkyloxy, a substituted or unsubstituted C.G.-guanidinoalkyloxy, and a substituted or unsubstituted C.G.-guanidinoalkylcarboxy.

4. The prodrug of claim 2, wherein each of $R_3$, $R_7$, and $R_{12}$ are selected from the group consisting of a substituted or unsubstituted C.G.-aminoalkyl, a substituted or unsubstituted C.G.-aminoalkyloxy, a substituted or unsubstituted C.G.-aminoalkylcarboxy, a substituted or unsubstituted C.G.-aminoalkyloxyaminoalkyl-aminocarbonyl, a substituted or unsubstituted C.G.-aminoalkylaminocarbonyl, a substituted or unsubstituted C.G.-aminoalkylcarboxyamido, an C.G.-quaternary ammonium alkylcarboxy, C.G.-HN—HC($Q_5$)-$C(O)$—O—, C.G.-HN—HC($Q_5$)-$C(O)$—N(H)—, C.G.-azidoalkyloxy, C.G.-cyanoalkyloxy, a substituted or unsubstituted C.G.-guanidinoalkyloxy, and a substituted or unsubstituted C.G.-guanidinoalkylcarboxy.

5. The prodrug of claim 2, wherein each of $R_3$, $R_7$, and $R_{12}$ are selected from the group consisting of C.G.-aminoalkyloxy and C.G.-aminoalkylcarboxy.

6. The prodrug of claim 2, wherein each of $R_3$, $R_7$, and $R_{12}$ are C.G.-aminoalkyloxy, and the alkyl portion is $C_1$-$C_4$.

7. The prodrug of claim 2, wherein C.G. is a sulfoalkyl group bonded to the amino terminal such that an alkyl portion of the sulfoalkyl group is bonded to the terminal amino and a sulfo portion of the sulfoalkyl group is terminal.

8. The prodrug of claim 7, wherein C.G. is a sulfomethyl group.

9. The prodrug of claim 1, wherein the CSA compound has a structure according to formula II:

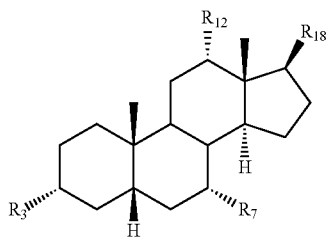

(II)

wherein, $R_3$ is selected from the group consisting of: hydroxy, optionally substituted $C_{1-18}$ alkoxy, optionally substituted amino, optionally substituted $C_{1-18}$ alkylamido, optionally substituted $C_{1-18}$ alkylureayl, optionally substituted $C_{1-18}$ alkylcarboxy, and optionally substituted ureayl;

$R_7$ is selected from the group consisting of: H, hydroxy, optionally substituted $C_{1-18}$ alkoxy, optionally substituted amino, optionally substituted $C_{1-18}$ alkylamido, optionally substituted $C_{1-18}$ alkylureayl and optionally substituted $C_{1-18}$ alkylcarboxy;

$R_{12}$ is selected from the group consisting of: H, hydroxy, optionally substituted $C_{1-18}$ alkoxy, optionally substituted amino, optionally substituted $C_{1-18}$ alkylamido, optionally substituted $C_{1-18}$ alkylureayl, optionally substituted $C_{1-18}$ alkylcarboxy, and optionally substituted ureayl; and $R_{18}$ is selected from the group consisting of: H, optionally substituted $C_{1-18}$ alkyl, and —$R_{20}$—(C=O)—N—$R_{21}R_{22}$, where, $R_{20}$ is omitted or substituted or unsubstituted alkyl, alkenyl, alkynyl, or aryl, and $R_{21}$ and $R_{22}$ are independently selected from the group consisting of hydrogen, substituted or unsubstituted alkyl, substituted or unsubstituted alkenyl, substituted or unsubstituted alkynyl, or substituted or unsubstituted aryl, provided that at least one of $R_{21}$ and $R_{22}$ is not hydrogen.

10. The prodrug of claim 9, where, $R_{20}$ is omitted or substituted or unsubstituted $C_1$-$C_{10}$ alkyl, substituted or unsubstituted $C_1$-$C_{10}$ alkenyl, substituted or unsubstituted $C_1$-$C_{10}$ alkynyl, or substituted or unsubstituted $C_6$ or $C_{10}$ aryl, and $R_{21}$ and $R_{22}$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_7$-$C_{13}$ aralkyl, optionally substituted (5 to 10 membered heteroaryl)-$C_1$-$C_6$ alkyl, optionally substituted $C_3$-$C_{10}$ carbocyclyl, optionally substituted $C_4$-$C_{10}$ (carbocyclyl)alkyl, optionally substituted (5 to 10 membered heterocyclyl)-$C_1$-$C_6$ alkyl, optionally substituted amido, and amine protecting group.

11. The prodrug of claim 9, wherein $R_{21}$ and $R_{22}$, together with the atoms to which they are attached, form an optionally substituted 5 to 10 membered heterocyclyl ring.

12. The prodrug of claim 1, wherein the prodrug is selected from the group consisting of:

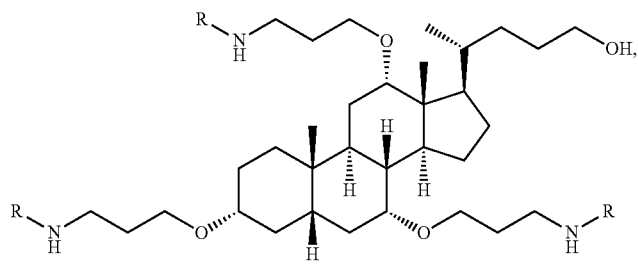

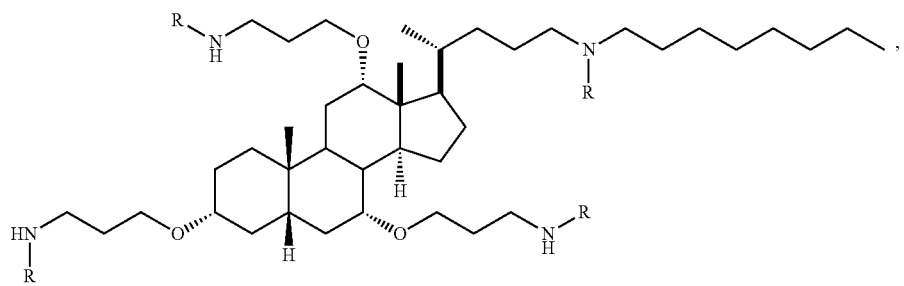

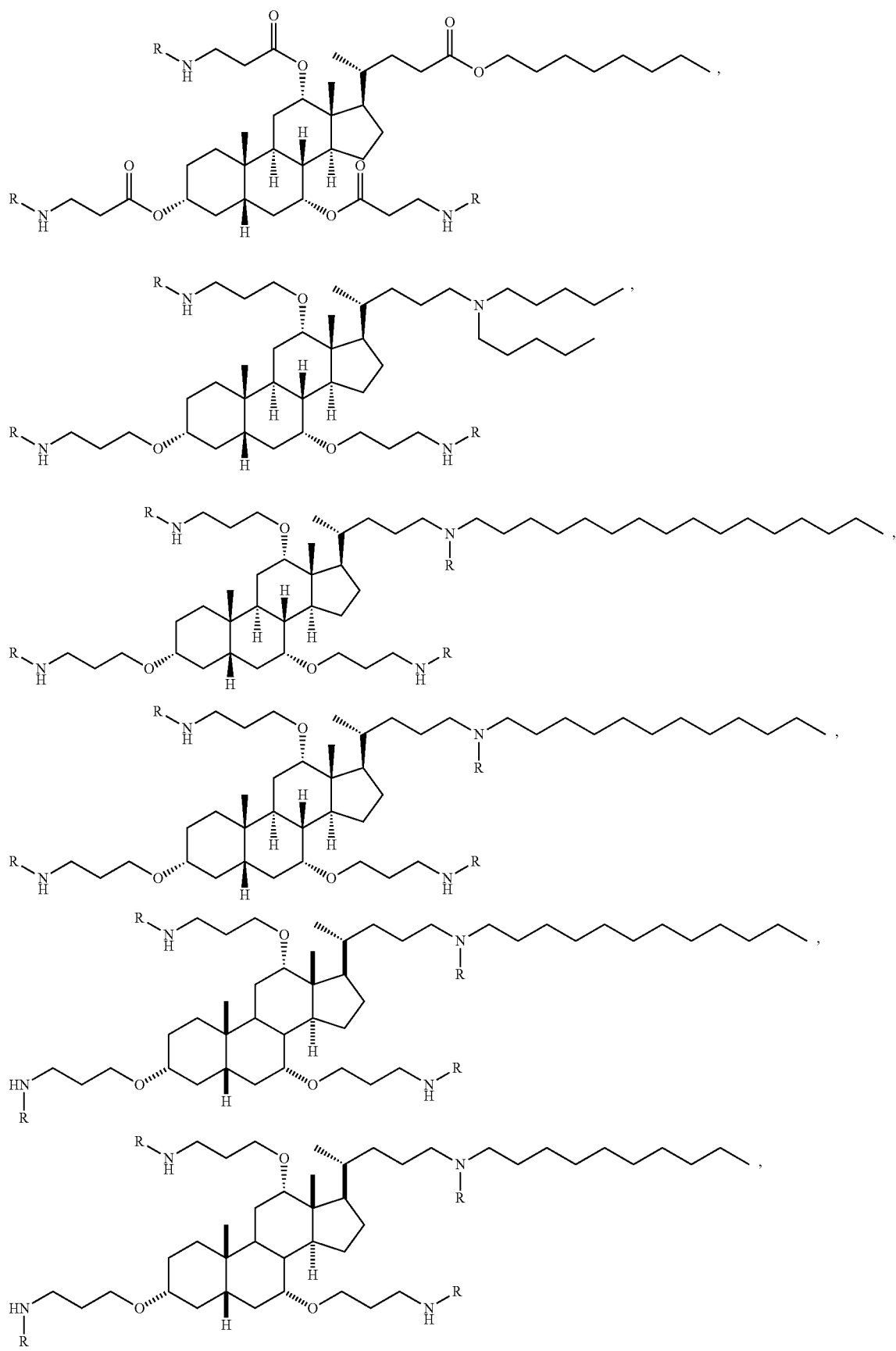

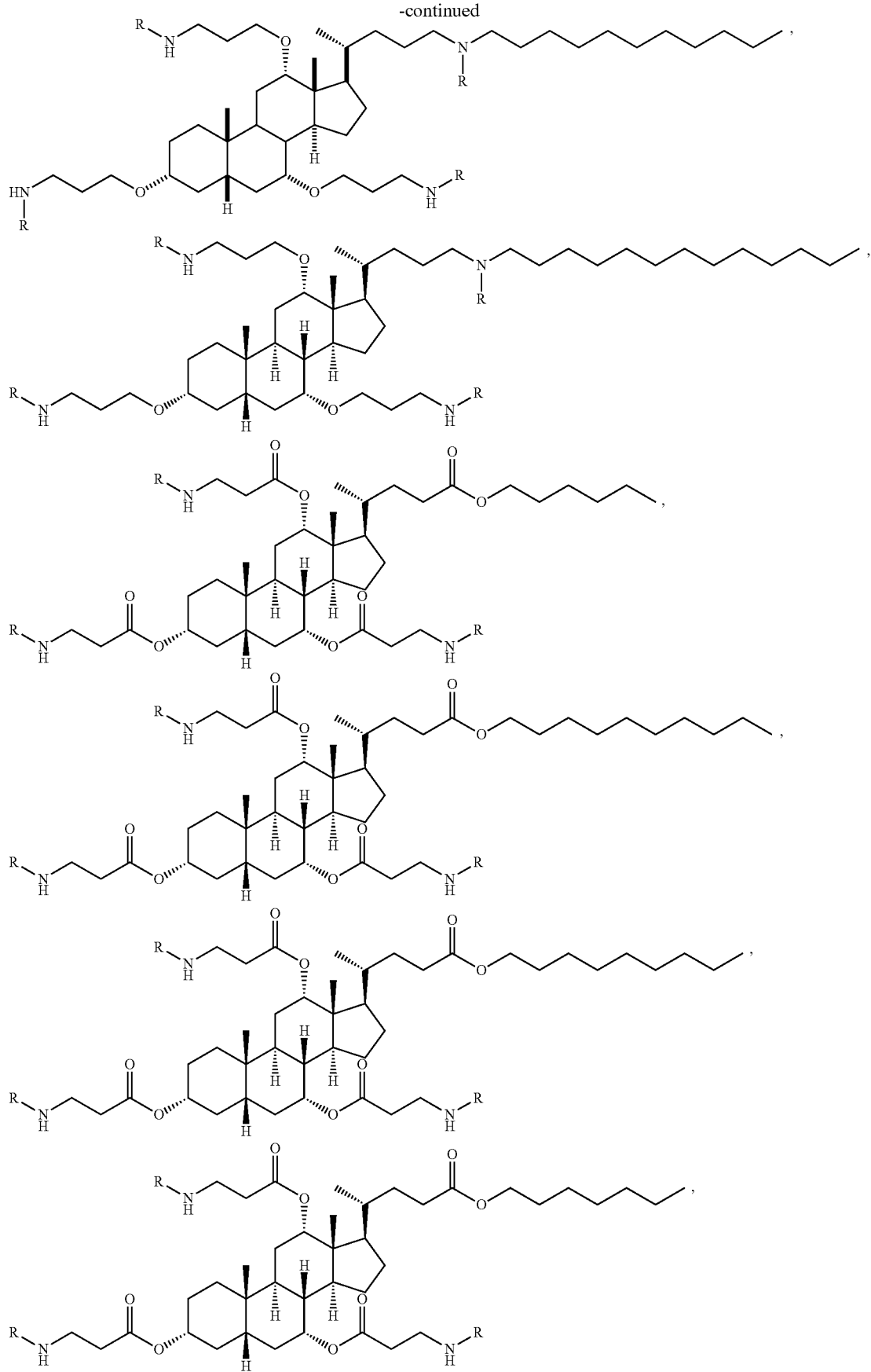

-continued
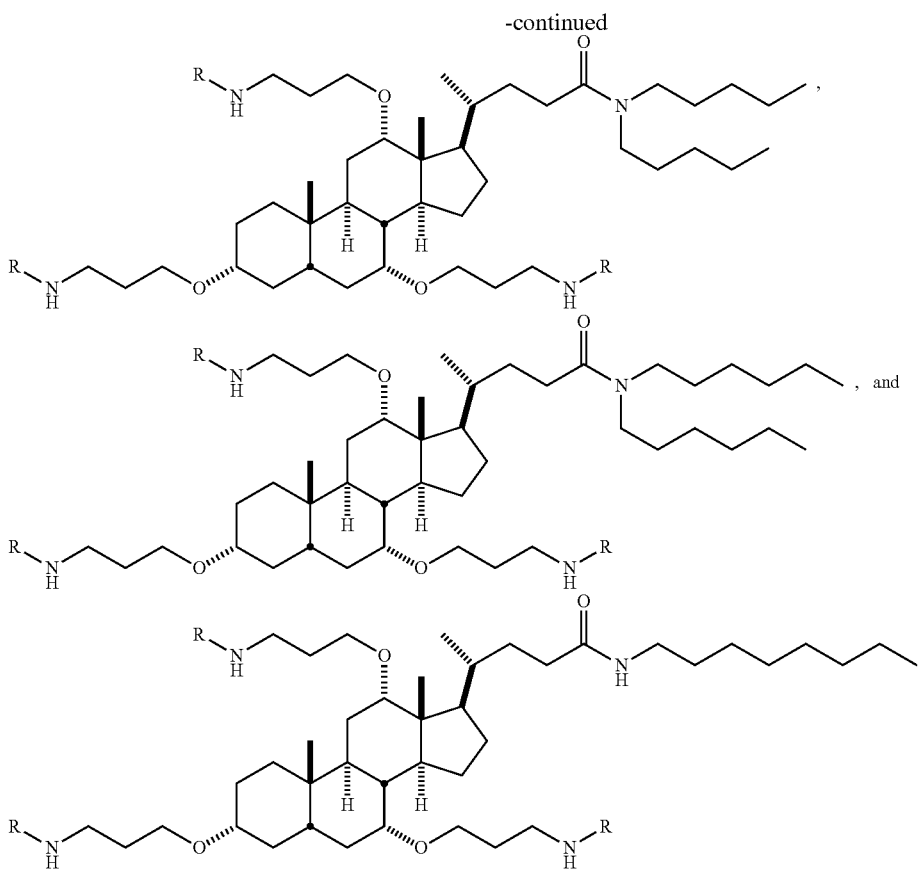
wherein R is a cleavable group selected from the group consisting of $CH_2SO_3^-$ or salt thereof, with a $CH_2$ portion of the cleavable group being bonded to the terminal amine.
13. The prodrug of claim 1, wherein B is a sulfomethyl group.
14. The prodrug of claim 1, wherein A is selected from the group consisting of:
(CSA-8)
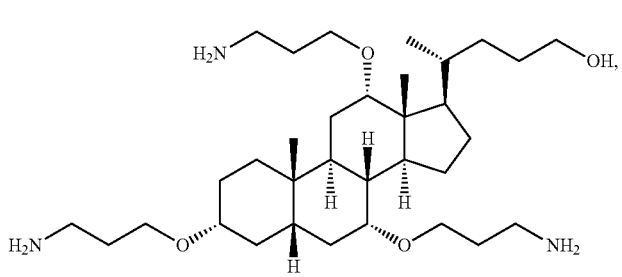
(CSA-13)
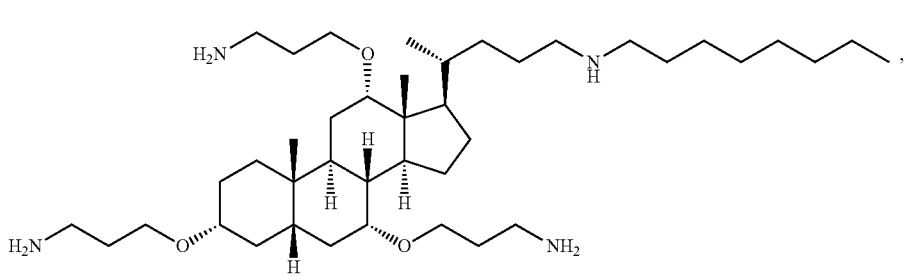

(CSA-44)
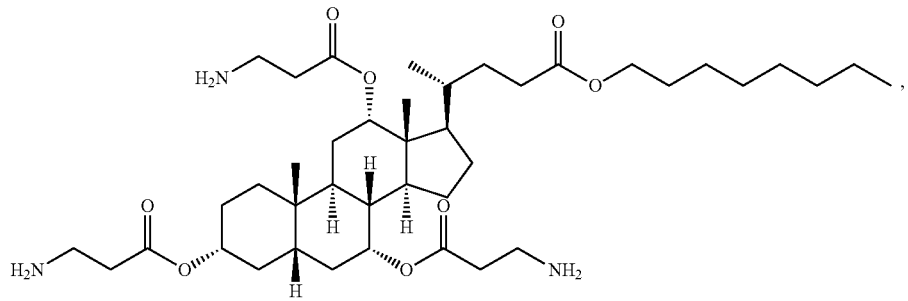
(CSA-90)
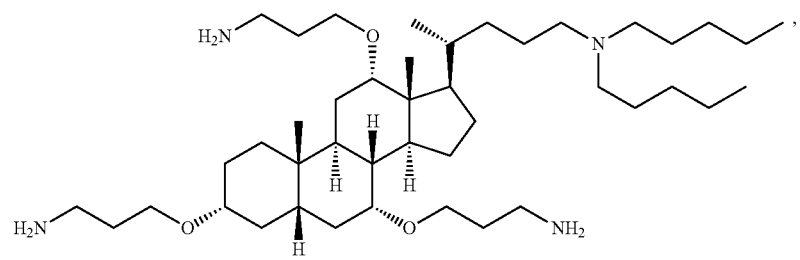
(CSA-92)
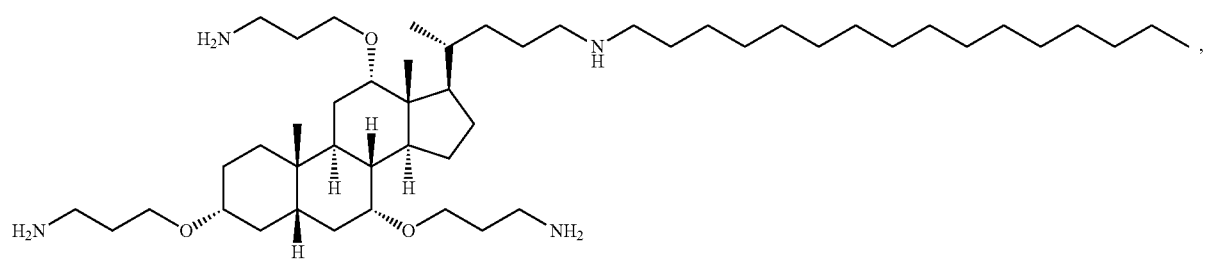
(CSA-131)
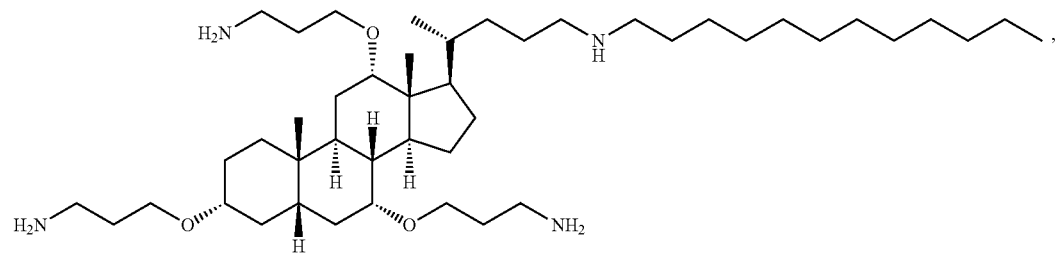
(CSA-134)
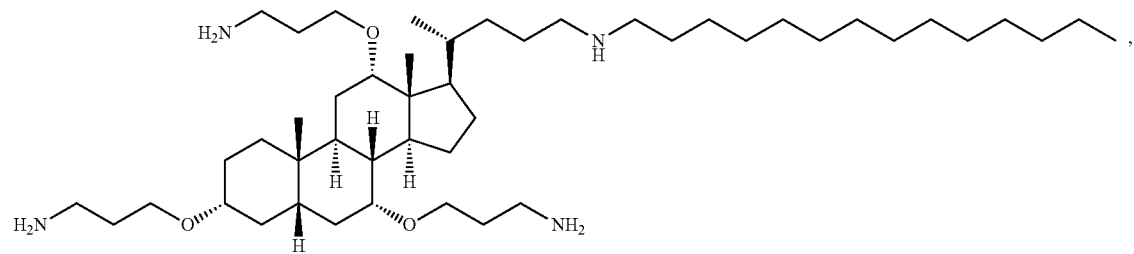
(CSA-136)
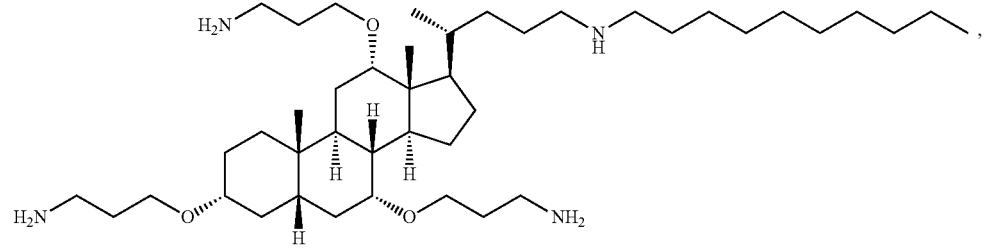

-continued
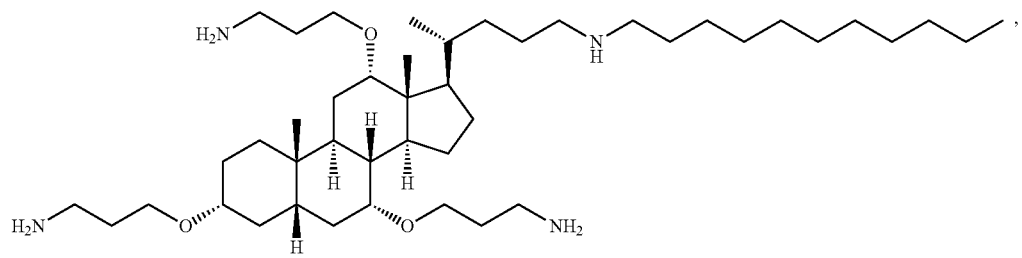
(CSA-137)
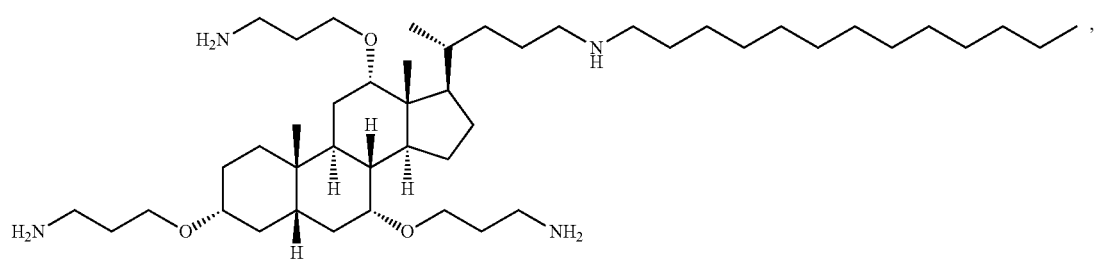
(CSA-138)
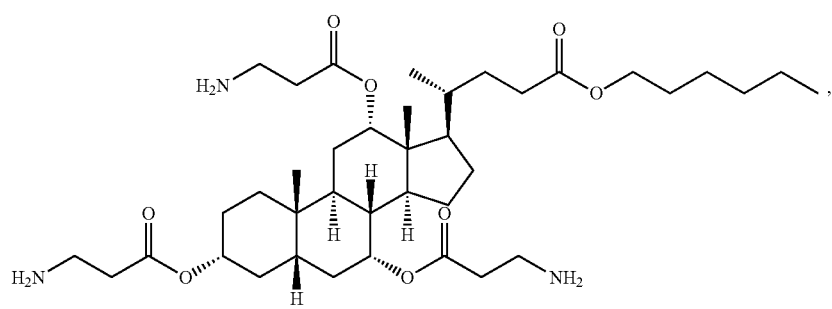
(CSA-142)
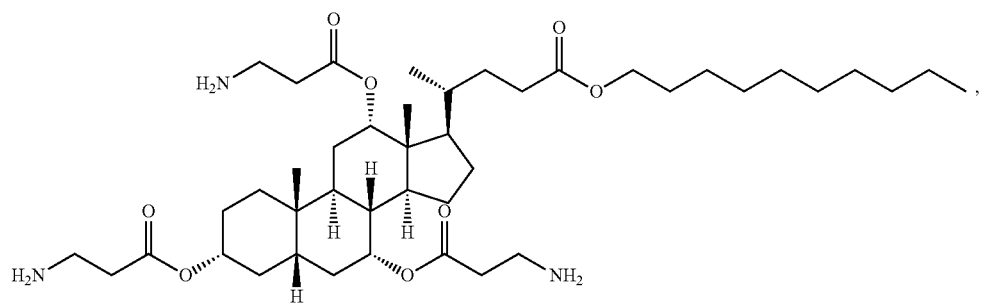
(CSA-144)

(CSA-145)
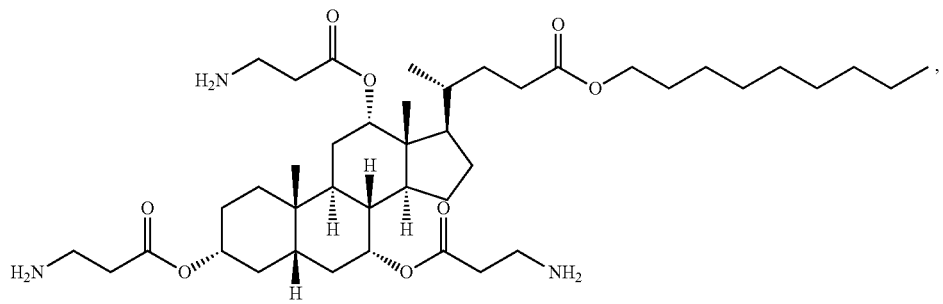
(CSA-146)
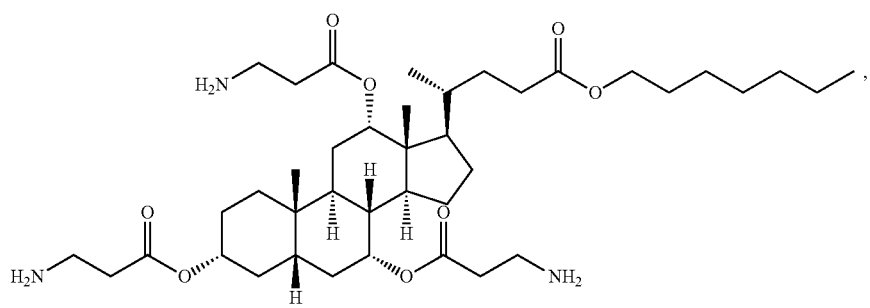
(CSA-190)
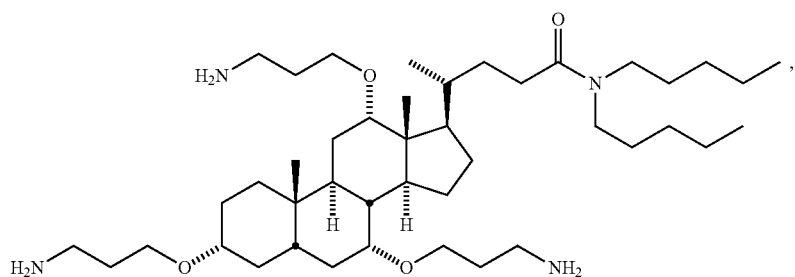
(CSA)-191
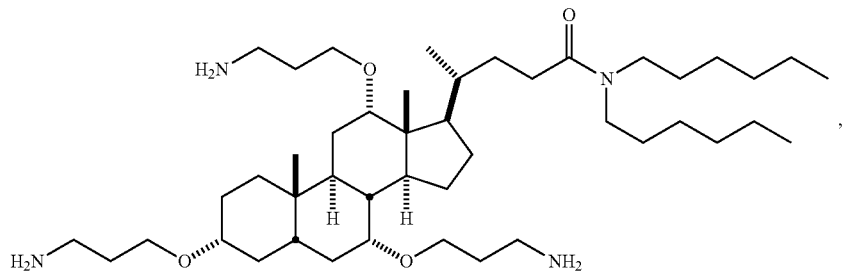

(CSA-192)

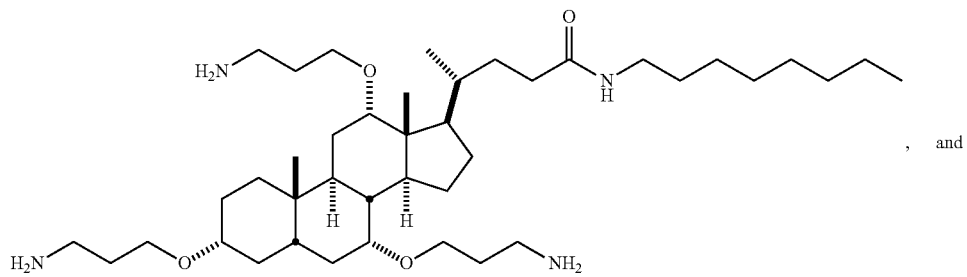

, and and pharmaceutically acceptable salts thereof, stereoisomers thereof, solvates thereof, and polymorphs thereof.

15. The prodrug of claim 1, wherein the prodrug comprises:

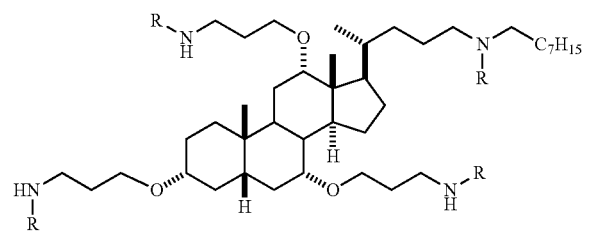

and wherein R is a cleavable group selected from the group consisting of $CH_2SO_3^-$ or salt thereof.

16. The prodrug of claim 1, wherein the prodrug comprises:

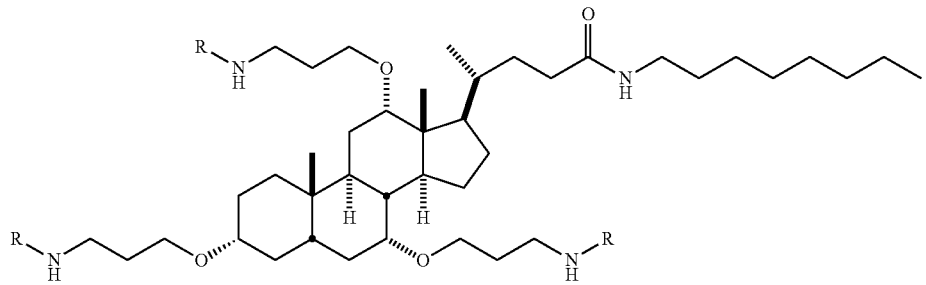

and wherein R is a cleavable group selected from the group consisting of $CH_2SO_3^-$ or salt thereof.

17. The prodrug of claim 1, wherein B is a group that is hydrolyzed under acidic conditions.

18. The prodrug of claim 1, wherein the C.G. is sensitive to and is altered or removed by at least one of ligase, isomerase, lyase, transferase, hydrolase, or oxidoreductase enzymes.

19. The prodrug of claim 1, wherein the C.G. is sensitive to and is altered or removed by at least one of change in pH, temperature, ionic conditions, or water content.

20. The prodrug of claim 1, wherein the C.G. is attached via a hydrolysable connection.

21. The prodrug of claim 1, wherein C.G. is removable or alterable upon contact of the CSA prodrug with other ingredients during preparation of a pharmaceutical formulation.

22. A pharmaceutical composition, comprising the prodrug of claim 1 and at least one pharmaceutically acceptable carrier or diluent.

23. The pharmaceutical composition of claim 22, further comprising at least one additional therapeutic agent.

24. The pharmaceutical composition of claim 23, wherein the at least one additional therapeutic agent is selected form the group consisting of anti-bacterial agents, anti-fungal agents and anti-inflammatory agents.

25. The pharmaceutical composition of claim 22, wherein the composition is formulated into a dosage form selected from the group consisting of: capsule, soft-gelatin capsule, tablet, suspension, injectable, liposomal delivery device, surface-coated liposomal delivery device, suppository, powder and liquid.

26. A method for treating a subject suffering from a bacterial or fungal infection comprising administering to the patient the pharmaceutical composition of claim 22.

27. A method for treating a subject suffering from cystic fibrosis comprising administering to the patient the pharmaceutical composition of claim 22.

28. A method for treating a subject suffering from a multiple myeloma comprising administering to the patient the pharmaceutical composition of claim 22.

29. A medical device for placement in a subject in need of treatment having inside and outside surfaces and at least one of inside and the outside surfaces being coated with a drug release coating comprising the prodrug of claim 1 and at least one pharmaceutically acceptable carrier or diluent, the drug release coating being effective to release a therapeutically desired amount of the prodrug to the subject in need.

* * * * *

UNITED STATES PATENT AND TRADEMARK OFFICE
CERTIFICATE OF CORRECTION

| | | |
|---|---|---|
| PATENT NO. | : 10,155,788 B2 | Page 1 of 1 |
| APPLICATION NO. | : 14/875953 | |
| DATED | : December 18, 2018 | |
| INVENTOR(S) | : Paul B. Savage | |

It is certified that error appears in the above-identified patent and that said Letters Patent is hereby corrected as shown below:

On the Title Page

Page 3
Item (56), References Cited, Other Publications, change "Li et al; "Incremental conversin of Outer-Membrane Permeabilizers into Potent Antibiotics for Gram-Negative Bacteria", J. Am. Chem. Soc. 1999, 121, 9310-940." to –Li et al; "Incremental Conversion of Outer-Membrane Permeabilizers into Potent Antibiotics for Gram-Negative Bacteria", J. Am. Chem. Soc. 1999, 121, 931-940.–

In the Specification

Column 4
Line 67, change "cyclodecyl and cyclododecyl, cyclohexenyl" to –cyclodecyl, cyclododecyl, and cyclohexenyl–

Column 5
Line 31, change "example" to –example.–

Column 49
Line 6, change "One" to –On–

Signed and Sealed this
Nineteenth Day of November, 2019

Andrei Iancu
*Director of the United States Patent and Trademark Office*